(12) United States Patent
Sauter et al.

(10) Patent No.: US 8,101,352 B2
(45) Date of Patent: Jan. 24, 2012

(54) DETECTION OF ESR1 AMPLIFICATION IN BREAST CANCER

(75) Inventors: Guido Sauter, Hamburg (DE); Ronald Simon, Kaltenkirchen (DE); Phillip Stahl, Hamburg (DE); Frederik Holst, Hamburg (DE); Khawla Al-Kuraya, Riyadh (SA); Christian Ruiz, Basel (CH)

(73) Assignee: Universitatsklinikum Hamburg-Eppendorf, Hamburg (DE)

( * ) Notice: Subject to any disclaimer, the term of this patent is extended or adjusted under 35 U.S.C. 154(b) by 0 days.

(21) Appl. No.: 12/305,258

(22) PCT Filed: Jun. 26, 2007

(86) PCT No.: PCT/EP2007/056384
§ 371 (c)(1),
(2), (4) Date: Dec. 21, 2009

(87) PCT Pub. No.: WO2008/000749
PCT Pub. Date: Jan. 3, 2008

(65) Prior Publication Data
US 2010/0086915 A1    Apr. 8, 2010

(30) Foreign Application Priority Data

Jun. 26, 2006 (EP) .................................. 06116106

(51) Int. Cl.
*C12Q 1/68* (2006.01)
(52) U.S. Cl. ........................................................ 435/6.1
(58) Field of Classification Search .................... None
See application file for complete search history.

(56) References Cited

U.S. PATENT DOCUMENTS 5,292,638 A    3/1994   Benz et al.
2005/0153319 A1*   7/2005   Housman et al. ................. 435/6

FOREIGN PATENT DOCUMENTS

WO   WO-02/057283    7/2002
WO   WO-2005/028681   3/2005
WO   WO-2006/052731   5/2006

OTHER PUBLICATIONS

Nembrot et al. (Biochem Biophys Res Commun. Jan. 30, 1990;166(2):601-7).*
Sharma et al. (Sharma. Breast (1996), pp. 344-350).*
Koh et al. (Anticancer Res. Nov.-Dec. 1989;9(6):1841-5).*
Al-Kuraya et al. Prognostic relevance of gene amplifications and coamplifications in breast cancer, *Cancer Res.*, 64:8534-40 (2004).
Andersen et al., Immunohistochemical estrogen receptor determination in paraffin-embedded tissue. Prediction of response to hormonal treatment in advanced breast cancer, *Cancer*, 64:1901-8 (1989).
Brandt et al., Double-differential PCR for gene dosage estimation of erbB oncogenes in benign and cancer tissues and comparison to cellular DNA content, *Gene*, 159:29-34 (1995).
Brandt et al., Isolation of blood-borne epithelium-derived c-erbB-2 oncoprotein-positive clustered cells from the peripheral blood of breast cancer patients, *Int J. Cancer*, 76:824-8 (1998).
Cherif et al., Detection of single-copy genes by nonisotopic in situ hybridization on human chromosomes, *Hum. Genet.*, 81:358-62 (1989).
Cowley et al., A comparison of transcriptional activation by ER alpha and ER beta, *J. Steroid Biochem. Mol. Biol.*, 69:165-75 (1999).
Deroo et al., Estrogen receptors and human disease, *J. Clin Invest.*, 116:561-70 (2006).
Diagnostik, *Therapie und Nachsorge des Mammakarzinoms der Frau*, Deutsche Krebsgesellschaft N.V. (Jul. 2004). [German only].
Elston et al., Pathological prognostic factors in breast cancer. I. The value of histological grade in breast cancer: experience from a large study with long-term follow-up, *Histopathology*, 19:403-10 (1991).
Fasco et al., Quantitation of estrogen receptor mRNA and ita alternatively spliced mRNAs in breast tumor cells and tissues, *Anal. Biochem.*, 245:167-78 (1997).
Fritz et al., Microarray-based copy number and expression profiling in dedifferentiated and pleomorphic liposarcoma, *Cancer Res.*, 62:2993-8 (2002).
Gradishar, Tamoxifen—what next?, *Oncologist*, 9:378-84 (2004).
Grunweller et al., RNA interference as a gene-specific approach for molecular medicine, *Curr. Med. Chem.*, 12:3143-61 (2005).
Harvey et al., Estrogen receptor status by immunohistochemistry is superior to the ligand-binding assay for predicting response to adjuvant endocrine therapy in breast cancer, *J. Clin. Oncol.*, 17:1474-81 (1999).
Hyytinen et al., Improved technique for analysis of formalin-fixed, paraffin-embedded tumors fluorescence in situ hybridization, *Cytometry*, 16:93-9 (1994).
Jarvinen et al., Amplification and deletion of topoisomerase IIalpha associate with ErbB-2 amplification and affect sensitivity to topoisomerase II inhibitor doxorubicin in breast cancer, *Am. J. Pathol.*, 156:839-47 (2000).
Kallioniemi et al., Comparative genomic hybridization for molecular cytogenetic analysis of solid tumors, *Science*, 258:818-21 (1992).
Kelloff et al., New science-based endpoints to accelerate oncology drug development, *Eur. J. Cancer*, 41:491-501 (2005).
Kung et al., Efficacy and safety of raloxifene 60 milligrams/day in postmenopausal Asian women, *J. Clin. Endocrinol. Metab.*, 88:3130-6 (2003).
Lancaster et al., BRCA 1 and 2—a genetic link to familial breast and ovarian cancer, *Medscape Womens Health*, 2:7 (1997).
Lawson et al., Low oestrogen receptor alpha expression in normal breast tissue underlies low breast cancer incidence in Japan, *Lancet*, 354:1787-8 (1999).

(Continued)

*Primary Examiner* — Christopher M. Babic
(74) *Attorney, Agent, or Firm* — Marshall, Gerstein & Borun LLP

(57) ABSTRACT

The present invention relates to an in-vitro method of identifying a tumor resulting from a proliferative breast disease as responsive to anti-estrogen treatment. Further, the invention relates to an in-vitro method of identifying a candidate patient with a proliferative breast disease as suitable for anti-estrogen treatment. In a further aspect, the invention provides an in-vitro method of identifying an individual with a non-cancerous proliferative breast disease who is at risk of developing breast cancer. The invention also provides kits for performing the above methods.

19 Claims, 4 Drawing Sheets

OTHER PUBLICATIONS

Mansur et al., Genetic polymorphisms of estrogen receptors in patients with premature coronary artery disease, *Arch. Med. Res.*, 36:511-7 (2005).

Masood et al., Reproducibility of LSI HER-2/neu SpectrumOrange and CEP 17 SpectrumGreen Dual Color deoxyribonucleic acid probe kit. For enumeration of gene amplification in paraffin-embedded specimens: a multicenter clinical validation study, *Ann. Clin. Lab. Sci.*, 28:215-23 (1998).

Matsui et al., P450 aromatase inhibiton assay using a competitive ELISA, *J. Pharm. Biomed. Anal.*, 38:307-12 (2005).

Melnick et al., The theoretical bases of transcriptional therapy of cancer: can it be put into practice?, *J. Clin. Oncol.*, 23:3957-70 (2005).

Modugno et al., Allelic variants of aromatase and the androgen and estrogen receptors: toward a multigenic model of prostate cancer risk, *Clin. Cancer Res.*, 7:3092-6 (2001).

Morris et al., Fulvestrant ('Faslodex')—a new treatment option for patients progressing on prior endrocrine therapy, *Endocr. Relat. Cancer*, 9:267-76 (2002).

Murphy et al., Novel mutations in the estrogen receptor messenger RNA in human breast cancers, *J. Clin. Endocrinol. Metab.*, 81:1420-7 (1996).

Naidu et al., Expression and amplification of cyclin D1 in primary breast carcinomas: relationship with histopathological types and clinico-pathological parameters, *Oncol. Rep.*, 9:409-16 (2002).

Current Status of Test Methods for Detecting Endocrine Disruptors: In Vitro Estrogen Receptor Binding Assays, *National Institutes of Health Publication No. 03-4504* (2002).

Nembrot et al., Estrogen receptor gene amplification is found in some estrogen receptor-positive human breast tumors, *Biochem. Biophys. Res. Commun.*, 166:601-7 (1990).

O'Connell, Genetic and cytogenetic analyses of breast cancer yield different perspectives of a complex disease, *Breast Cancer Res. Treat.*, 78:347-57 (2003).

Omoto et al., Estrogen receptor (ER) beta1 and ERbetacx/beta2 inhibit ERalpha function differently in breast cancer cell line MCF7, *Oncogene*, 22:5011-20 (2003).

Palmberg et al., Androgen receptor gene amplification at primary progression predicts response to combined androgen blockade as second line therapy for advanced prostate cancer, *J. Urol.*, 164:1992-5 (2000).

Pauletti et al., Detection and quantitation of HER-2/neu gene amplification in human breast cancer archival material using fluorescence in situ hybridization, *Oncogene*, 13:63-72 (1996).

Pegram et al., Results of two open-label, multicenter phase II studies of docetaxel, platinum salts, and trastuzumab in HER2-positive advanced breast cancer, *J. Natl. Cancer Inst.*, 96:759-69 (2004).

Peters et al., Estrogen receptor domains E and F: role in dimerization and interaction with coactivator RIP-140, *Mol. Endocrinol.*, 13:286-96 (1999).

Poola et al., Quantitation of estrogen receptor mRNA copy numbers in breast cancer cell lines and tumors, *Anal. Biochem.*, 258:209-15 (1998).

Poola, Molecular assay to generate expression profile of eight estrogen receptor alpha isoform mRNA copy numbers in picogram amounts of total RNA from breast cancer tissues, *Anal. Biochem.*, 314:217-26 (2003).

Press et al., Evaluation of HER-2/neu gene amplification and overexpression: comparison of frequently used assay methods in a molecularly characterized cohort of breast cancer specimens, *J. Clin. Oncol.*, 20:3095-105 (2002).

Puddefoot et al., Non-competitive steroid inhibition of oestrogen receptor functions, *Int. J. Cancer*, 101:17-22 (2002).

Ruiz et al., Tissue microarrays for comparing molecular features with proliferation activity in breast cancer, *Int. J. Cancer*, 118:2190-4 (2006).

Scandinavian Breast Group Trial 9401, Topoisomerase IIalpha gene amplification predicts favorable treatment response to tailored and dose-escalated anthracycline-based adjuvant chemotherapy in HER-2/neu-amplified breast cancer: Scandinavian Breast Group Trial 9401, *J. Clin. Oncol.*, 24:2428-36 (2006).

Schrag et al., Life expectancy gains from cancer prevention strategies for women with breast cancer and BRCA1 or BRCA2 mutations, *JAMA*, 283:617-24 (2000).

Schuur et al., Monoallelic amplification of estrogen receptor-alpha expression in breast cancer, *Cancer Res.*, 60:2598-601 (2000).

Seshadri et al., Cyclin DI amplification is not associated with reduced overall survival in primary breast cancer but may predict early relapse in patients with features of good prognosis, *Clin. Cancer Res.*, 2:1177-84 (1996).

Simon et al., Tissue microarrays, Chapter 26 IN: Roulston et al. (eds.), *Molecular Diagnosis of Cancer*, Humana Press Inc. (2004).

Solinas-Toldo et al., Matrix-based comparative genomic hybridization: biochips to screen for genomic imbalances, *Genes Chromosomes Cancer*, 20:399-407 (1997).

Stierer et al., Immunohistochemical and biochemical measurement of estrogen and progesterone receptors in primary breast cancer. Correlation of histopathology and prognostic factors, *Ann. Surg.*, 218:13-21 (1993).

Tanner et al., Topoisomerase II α gene amplification predicts favorable treatment response to tailored and dose-escalated anthracycline-based adjuvant chemotherapy in *HER-2/neu*-amplified breast cancer: Scandinavian Breast Group Trial 9401, *J. Clin. Oncol.*, 24:2428-36 (2008).

Tavassoli et al., WHO histological classification of tumours of the breast, WHO/IARC Classification of Tumours (2003).

Torhorst et al., Tissue microarrays for rapid linking of molecular changes to clinical endpoints, *Am. J. Pathol.*, 159:2249-56 (2001).

Vona et al., Isolation by size of epithelial tumor cells : a new method for the immunomorphological and molecular characterization of circulating tumor cells, *Am. J. Pathol.*, 156:57-63 (2000).

Wagner et al., Chromosome 8p deletions are associated with invasive tumor growth in urinary bladder cancer, *Am. J. Pathol.*, 151:753-9 (1997).

Wong et al., Detection of circulating tumour cells with the magnetic activated cell sorter, *Br. J. Surg.*, 82:1333-7 (1995).

Wittekind et al., *Tnm Atlas: Illustrated Guide to the Tnm/Ptnm—Classification of Malignant Tumors*, Berlin: Springer Verlag (2005). English translated abstract provided, Abstract Only.

\* cited by examiner

Figure 2A

| | | on array (n) | ESR1 amplification | | | ER expression* | | |
|---|---|---|---|---|---|---|---|---|
| | | | analyzable (n) | amplification | p | analyzable (n) | expression | p |
| Cancers | all | 2197 | 1679 | 31.3% | | 2018 | 76.6% | |
| Histology | ductal carcinoma | 1552 | 1207 | 33.1% | | 1429 | 77.1% | |
| | lobular carcinoma | 312 | 207 | 29.5% | | 275 | 87.6% | |
| | mucinous carcinoma | 69 | 37 | 48.6% | 0.0012** | 61 | 93.4% | <0.0001** |
| | medullary carcinoma | 58 | 48 | 4.2% | <0.0001** | 52 | 17.3% | <0.0001** |
| | tubular carcinoma | 56 | 42 | 28.6% | | 48 | 89.6% | |
| | cribriform carcinoma | 65 | 55 | 32.7% | | 56 | 91.1% | |
| | papillary carcinoma | 30 | 27 | 22.2% | | 28 | 67.9% | |
| | others* | 79 | 56 | 16.1% | | 69 | 34.8% | |
| pT stage | pT1 | 820 | 578 | 34.4% | 0.0416 | 716 | 80.4% | 0.0020 |
| | pT2 | 1023 | 811 | 31.2% | | 948 | 73.2% | |
| | pT3 | 124 | 92 | 23.9% | | 114 | 72.8% | |
| | pT4 | 242 | 189 | 25.4% | | 229 | 80.3% | |
| Nodal stage | pN0 | 950 | 711 | 31.9% | 0.1397 | 849 | 78.1% | 0.1765 |
| | pN1 | 793 | 608 | 27.8% | | 726 | 75.6% | |
| | pN2 | 121 | 90 | 24.4% | | 113 | 70.8% | |
| BRE grade | G1 | 545 | 421 | 35.9% | <0.0001 | 522 | 92.9% | <0.0001 |
| | G2 | 844 | 685 | 34.2% | | 833 | 86.3% | |
| | G3 | 655 | 571 | 24.7% | | 661 | 51.9% | |

* according to Allred

Figure 2B

| Parameter | | p-value |
|---|---|---|
| pT stage | pT1-4 | 0.1294 |
| BRE grade | G1-3 | 0.0028 |
| pN stage | pN0-pN2 | 0.0039 |
| ER expression status | neg/pos (Allred score) | 0.1242 |
| ESR1 amplification status | amplified vs non-amplified | 0.0368 |

DETECTION OF ESR1 AMPLIFICATION IN BREAST CANCER

FIELD OF THE INVENTION

The present invention relates to an in-vitro method of identifying a tumor resulting from a proliferative breast disease as responsive to anti-estrogen treatment. Further, the invention relates to an in-vitro method of identifying a candidate patient with a proliferative breast disease as suitable for anti-estrogen treatment. In a further aspect, the invention provides an in-vitro method of identifying an individual with a non-cancerous proliferative breast disease who is at risk of developing breast cancer. The invention also provides kits for performing the above methods.

BACKGROUND OF THE INVENTION

Breast cancer is the leading malignancy in women, accounting for more than 350,000 deaths per year in western countries. On the molecular level, about 20% of breast cancers are characterized amplification of the gene encoding the HER2 growth factor receptor (Pauletti, G., et al. (1996), Oncogene, 13: 63-72). Amplification of the HER2 gene results in strong over-expression of the receptor protein and, in turn, confers a growth advantage to the tumor cells. Herceptin, a monoclonal antibody targeting the HER2 protein, improves patient survival even in metastatic breast cancers and is regarded as a paradigm for the potential of a new generation of gene specific drugs (Pegram, M. D., et al. (2004), J Natl Cancer Inst, 96: 759-769).

Amplification of genomic DNA is the result of a selection process aiming at facilitating tumor cell growth, e.g. by high level overexpression of genes that otherwise would be growth rate limiting. Amplified genes, therefore, are likely to be vitally important for tumor cells and represent particular attractive targets for new gene specific therapies. In breast cancer, more than 30 regions of amplification have been detected by means of classical comparative genomic hybridization (CGH), see for example, O'Connell, et al. (2003), Breast Cancer Res Treat, 78: 347-357. Numerous important oncogenes have been identified within these amplicons, for example CMYC at chromosome 8q24, EGFR at 7p21, or CCND1 at 11q13. However, it is assumed that the majority of genes which undergo amplification in breast malignancies has not yet been identified. Thus, there is a hope that other amplified genes can be used in diagnosis, estimation of prognosis and treatment of these diseases.

It has been surprisingly found in the course of the present invention that amplification of the ESR1 gene located at 6q25.1 and encoding the alpha isoform of the estrogen receptor appears to be the most frequent gene amplification that is detectable in breast cancer. In the experiments conducted by the inventors, amplification of the ESR1 gene was observed in 31% of the examined tumors. Even more importantly, the present invention provides evidence that amplification of the ESR1 gene is correlated to an enhanced susceptibility of a tumor, such as a breast cancer, to anti-estrogen treatment, e.g. by administration of Tamoxifen. As a consequence, detection of ESR1 amplification is of significant clinical relevance and may be used in diagnosis and estimation of prognosis and also as a tool for making decisions as to the specific treatment protocol to be used with a particular patient suffering from a proliferative breast disease such as breast cancer.

In view of the enormous number of publications dealing with the estrogen receptors and their relationship with breast cancer, it is surprising that ESR1 amplification in breast cancer has not been identified so far. The inability to detect the 6q25.1 amplicon in several hundreds of breast cancer samples analyzed by classical metaphase CGH during the last decade argues for a generally small amplicon size overstraining the classical CGH resolution. Because the experimental noise is often considerable in array hybridization experiments, single spot peaks are frequently seen and artifacts are difficult to distinguish from true amplification events. In order to overcome these shortcomings, the experiments of the present invention specifically focused on small single gene amplifications. By fluorescence in situ hybridization using a probe specific for the ESR1 gene, putative ESR1 amplification events previously seen in the CGH assay were confirmed.

DESCRIPTION OF THE FIGURES

FIG. 2A shows a table demonstrating the association of ESR1 copy number changes and breast cancer phenotype. FIG. 2B shows the contribution of potential prognostic factors to tumor specific survival in breast cancer patients that received Tamoxifen monotherapy (multivariate COX regression model).

SUMMARY OF THE INVENTION

Figure 1:
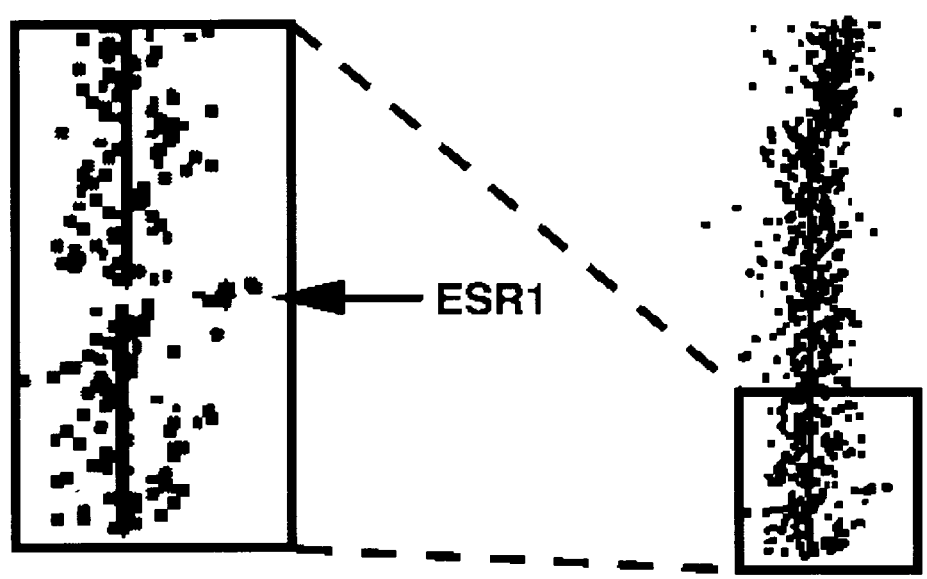
FIG. 1 depicts a plot from the CGH experiment showing amplification of the ESR1 gene as indicated by the arrow.

Estrogens belong to the group of steroid hormones. The three major naturally occurring estrogens in women are estradiol, estriol and estrone. From puberty to menopause, estrogen production mainly takes place in the ovaries. After menopause, when the ovaries no longer produce estrogens, body fat is the primary source for these hormones. Like other steroid hormones, estrogens act as signalling molecules and exhibit their function by binding to estrogen receptors which are present inside cells of those tissues which are targets for estrogen regulation. Two different human estrogen receptors occur which are designated estrogen receptor alpha isoform (or ER-alpha) and estrogen receptor beta isoform (ER-beta). The isoforms are encoded by different genes, ESR1 and ESR2, respectively, which are found at different chromosomal locations, and numerous mRNA splice variants exist for both receptors in both diseased and normal tissue (see for example, Deroo & Korach (2006), Journal of Clinical Investigation 116: 561-570).

Like all steroid receptors, the estrogen receptors (i.e. the alpha and beta isoform) exhibit a modular structure, with discrete regions of the protein (domains) responsible for transcriptional activation, DNA binding, nuclear localization, ligand binding, and dimerization (see Peters and Khan (2003), Mol Endocrin 13(2):286-296). ER-alpha and ER-beta share a high degree of homology in the ligand binding (AF-2) and DNA-binding domains, but differ in the activation function (AF-1) domain. Comparison of the AF-1 domains suggests that the activity on estrogen response elements is much stronger in ER-alpha as compared to ER-beta (Cowley, S. M., et al. (1999), J Steroid Biochem Mol Biol 69: 165-175). Although comparatively little is known about the function and clinical significance of ER-beta, it is generally believed that ER-beta counteracts the function of ER-alpha and leads to a reduction of estrogen-stimulated proliferation (Omoto, Y., et al. (2003), Oncogene 22: 5011-5020).

The human estrogen receptor alpha is encoded by the ESR1 gene which maps to 6q25.1 of human chromosome 6. The nucleotide sequence of SEQ ID NO:1 shows the ESR1 coding sequence as defined by nucleotides 1048135 to 1343855 together with approximately 1 Mb of sequence located upstream (at the 5' end of the sequence) of the coding sequence and approximately 1.38 Mb of sequence located downstream (at the 3' end of the sequence) of the coding sequence. As used herein, the terms "ESR1 gene" and "ESR1 coding sequence" are used interchangeably and refer to the genomic sequence (containing exons and introns) which is transcribed and spliced to the mRNA depicted in SEQ ID NO:2 without promoter and enhancer structures which might be associated to this DNA entity. The ESR1 gene sequence is also available under NCBI GenBank ID NT_025741.14, providing the assembled nucleotide sequence of human chromosome 6. In the sequence portion designated "Human Genome Build 36", the ESR1 gene covers nucleotides 152170379 to 152466099. The ESR1 gene comprises several introns which are spliced out after transcription. The nucleotide sequence of the spliced ESR1 mRNA sequence is depicted in SEQ ID NO:2 and is available under NCBI GenBank ID NM_000125. The corresponding amino acid sequence of the estrogen receptor alpha protein is depicted in SEQ ID NO:3 and is also available under NCBI GenBank ID NM_000125. There are numerous allelic variants of the ESR1 gene, see for example, Modugno et al. 2001, Clin Cancer Res. 7(10):309 or Mansur Ade et al. 2005, Arch Med Res. 36(5):511.

The estrogen receptors (alpha or beta isoform) are normally located in the nucleus of the target cell. According to the accepted model of steroid hormone action, the estrogen receptors are in an inactive state in the absence of hormone. When estrogen passes into the nucleus, the estrogen receptors bind to estrogen. Upon estrogen binding, the receptors form dimers which then bind to estrogen response element DNA sequences directly or indirectly through protein-protein interactions with activator protein 1 (AP1) or SP1 sites in the promoter region of estrogen-responsive genes. This binding results in the recruitment of co-regulatory proteins (co-activators or co-repressors) to the promoter, thereby leading to an increased or decreased gene expression. The altered gene expression can influence cell behavior in different ways, depending on the tissue type involved. In some target tissues, such as breast tissue, the main effect of estrogen in healthy women is to induce cell proliferation. For instance, estrogen causes the proliferation of cells lining the milk glands in order to prepare milk production. Aside from homodimeric receptors consisting of two alpha units or two beta units, mixed dimers may also occur. Different tissues express the two isoforms in different proportions, and therefore have different responses to stimulation by estrogens.

Although the ability to promote proliferation of breast cells lies within the normal functions of the estrogen molecule, it is also associated with an increased risk of developing breast cancer (Lawson J. S., et al. (1999), Lancet 354:1787-1788). Once invasive cancerous breast cells have formed, it is highly undesirable to have signal molecules that trigger proliferation of these cancerous cells. Consequently, immunohistochemical detection of expression of the alpha isoform of the estrogen receptor is routinely performed in order to determine whether breast cancer cells of a given patient express estrogen receptor or not (Andersen, J. and Paulsen, H. S. (1989), Cancer, 64: 1901-1908).

It has been demonstrated that more than two thirds of breast cancers show expression of the alpha isoform of the estrogen receptor at the time of diagnosis (Stierer, M., et al. (1993), Ann Surg, 218: 13-21). These cancers are generally referred to as estrogen-receptor-positive or ER-positive. In the remaining breast cancer cases, no estrogen-receptor alpha protein can be detected in the cells. These cancers are estrogen-receptor-negative or ER-negative. ER-positive breast cancers are currently treated, inter alia, by anti-estrogen therapy using so-called selective estrogen receptor modulators (SERMs) and/or aromatase inhibitors. For example, an estrogen antagonist like Tamoxifen is frequently applied to the patient with ER-positive breast cancer, normally after surgical removal of the tumor.

With the methods according to the present invention, it is now possible to identify a subgroup within the group of ER-positive patients suffering from a proliferative breast disease, such as breast cancer, which show a particular good response to anti-estrogen therapy. It could be demonstrated that tumors of breast cancer patients that show amplification of the ESR1 gene on the genomic level exhibit a clearly enhanced response to anti-estrogen therapy with Tamoxifen. A shown in FIG. 4, the overall survival of these patients is significantly increased compared to patients with tumors not exhibiting ESR1 amplification. These patients are classified as particular suitable for anti-estrogen therapy, for example with Tamoxifen. This finding was unexpected because in prostate cancer, where the mechanism of hormone dependent growth is comparable to breast cancer, amplification of the gene encoding the androgen receptor leads to resistance to anti-hormone therapy (Palmberg C. (2000), J Urol, 164: 1992-1995). The methods of the present invention therefore allow prediction of the responsiveness of a tumor resulting from a proliferative breast disease to anti-estrogen treatment based on the evidence that the ESR1 gene is amplified. Such information can be useful in order to design an appropriate therapy schedule which is more tailored to the nature and molecular characteristics of the tumor. For example, in cases where a tumor shows a particularly responsiveness to anti-estrogen treatment, for example, administration of Tamoxifen, the patient can be subjected to an anti-estrogen monotherapy, without the need to apply a concurrent chemotherapy. Alternatively, where chemotherapy is still part of the therapy, it might be possible to reduce the dosis of the chemotherapeutic agents while maintaining the same treatment results.

Amplification of the ESR1 gene is regularly associated with co-amplification of genomic sequence portions that frame the ESR1 gene on the human chromosome. It has been shown in the present invention that it is possible to spot ESR1 gene amplification events both directly by detecting amplification of the ESR1 sequence and indirectly by detecting amplification of a nucleotide sequence which comprises the ESR1 gene. Thus, according to a first aspect of the invention, an in-vitro method of identifying a tumor which results from a proliferative breast disease as responsive to anti-estrogen treatment is provided. The method comprises the steps of
  a) detecting in a cell sample from said tumor whether a nucleotide sequence portion of the nucleotide sequence of SEQ ID NO:1 or a nucleotide sequence having at least 95% sequence identity to such portion is amplified in the genome of said tumor cells;
  b) classifying said tumor as responsive to anti-estrogen treatment, if the nucleotide sequence portion of SEQ ID NO:1 or a nucleotide sequence having at least 95% sequence identity to such portion is amplified in the genome of said tumor cells.

According to a second aspect of the invention, an in-vitro method of identifying a candidate patient with a tumor resulting from a proliferative breast disease as suitable for anti-estrogen treatment is provided. The method comprises the steps of
   a) detecting in a cell sample from said tumor whether a nucleotide sequence portion of the nucleotide sequence of SEQ ID NO:1 or a nucleotide sequence having at least 95% sequence identity to such portion is amplified in the genome of said tumor cells;
   b) classifying said patient as one that is suitable for anti-estrogen treatment, if the nucleotide sequence portion of the nucleotide sequence of SEQ ID NO:1 or a nucleotide sequence having at least 95% sequence identity to such portion is amplified in the genome of said tumor cells.

Accordingly, the invention also provides a method for treating a patient suffering from a tumor resulting from a proliferative breast disease, such as breast cancer, comprising the detection step a) indicated above, and subjecting the patient to an anti-estrogen treatment, if the nucleotide sequence portion of the nucleotide sequence of SEQ ID NO:1 or a nucleotide sequence having at least 95% sequence identity to such portion is amplified in the genome of said tumor cells. The present invention demonstrates for the first time that ESR1 amplification can not only be detected in breast cancer, but also in a significant part of benign proliferative breast diseases, such as ductal hyperplasia or ductal papillomas. Several genetic alterations in non-malignant breast lesions which are associated with an increased risk of developing cancer have been reported. For example, women with mutations of the BRCA1 and BRCA2 genes have a lifetime risk of breast cancer exceeding 80% and of ovarian cancer approaching 60% (Lancaster et al. (1997), Medscape Womens Health 2(2):7). Accordingly, prevention strategies including Tamoxifen treatment, bilateral prophylactic oophorectomy, or prophylactic contralateral mastectomy, have been shown to gain life expectancy (Schrag et al. (2000), JAMA 283(5):617).

Gene amplifications—like mutations—constitute genetic alterations. However, a gene amplification has so far never been demonstrated in a non-cancerous proliferative breast disease. Generally, amplifications modulate gene activity by massively overexpressing mRNA and resulting protein. In normal breast epithelial tissue, the function of the alpha isoform of the estrogen receptor resides in the reception and transduction of a signal facilitating epithelial cell proliferation. In the present invention, it was found that ESR1 amplification has a similar impact on cell proliferation in non-cancerous and cancerous proliferative breast diseases. Increased proliferation rates increase the risk to acquire additional genetic alterations and, in turn, the risk of developing breast cancer. Thus, ESR1 amplification can indicate a non-cancerous proliferative breast disease with an increased potential for malignant transformation. ESR1 amplification status analysis may serve as a prognostic marker in patients with ductal hyperplasia, ductal papillomas or other non-cancerous proliferative breast diseases described herein.

According to a further aspect, the invention therefore provides an in-vitro method of identifying an individual with a tumor resulting from a non-cancerous proliferative breast disease who is at risk of developing breast cancer. The methods comprises the steps of
   a) detecting in a cell sample from said tumor whether a nucleotide sequence portion of the nucleotide sequence of SEQ ID NO:1 or a nucleotide sequence having at least 95% sequence identity to such portion is amplified in the genome of said tumor cells;
   b) classifying said individual as one that is at risk of developing breast cancer, if the nucleotide sequence portion of the nucleotide sequence of SEQ ID NO:1 or a nucleotide sequence having at least 95% sequence identity to such portion is amplified in the genome of said tumor cells.

The methods according to the invention are in vitro methods which utilize samples comprising breast cells and/or breast tissue. The cells and tissues are derived from a breast region of concern, in particular from a tumor of the breast. The source of the tissue sample may be, for example, solid tissue from a fresh, frozen and/or preserved tissue sample, biopsy or aspirate. Preferably, the samples are derived from a breast biopsy. A breast biopsy involves removing breast cells or breast tissue for further molecular and/or histological examination. For example, breast biopsy samples are normally used to determine whether cancerous cells are present in the breast of a patient. Hitherto, biopsy and subsequent pathological analysis is the only definitive way to confirm, for example, breast cancer. Nevertheless, it is anticipated that the methods of the invention may also be conducted with blood samples. For this purpose, tumor cells are isolated from peripheral blood and subjected to amplification detection. Methods for tumor cell isolation from blood include filtration procedures ("Isolation by size of epithelial tumor cells (ISET)", described in Vona et al. (2000) Am J Pathol 156:57) or immunomagnetic (Brandt et al. (1998), Int J Cancer 76:824) or flow cytometric approaches (Wong et al. (1995), Br J Surg 82:1333). Furthermore, the methods of the invention may also be performed with cells obtained from bone marrow.

In the prior art, different methods of breast biopsy are known, for example, open excisional biopsy, needle biopsy (such as fine needle or core needle biopsy), or vacuum-assisted biopsy. These biopsy methods are well known in the art and have been described in numerous publications and standard textbooks (see for example "Diagnostik, Therapie and Nachsorge des Mammakarzinoms der Frau", Interdisziplinäre Leitlinie der Deutschen Krebsgesellschaft, published in June 2004). For example, open excisional biopsy (also referred to as open biopsy) is a surgical procedure, in which the tumor or lump is removed, either partly or completely, from the patient's breast and is further examined, for example, tested for malignancy. An open biopsy can be performed under local or general anesthesia. Prior to surgery, a radiologist often first marks the region of concern with a wire, thereby enabling the surgeon to find the location.

Fine needle biopsy is a percutaneous procedure in which fluid and/or small cell clusters are removed by use of a syringe equipped with a fine gauge needle (normally 20-25 gauge). In comparison, the needles used in core needle biopsy are somewhat larger (commonly 16-10 gauge), so that larger portions of breast tissue can be collected. In case the breast tissue region of concern, for example the tumor, is palpable, needle biopsy can be performed without guidance means. Otherwise, computer-based stereotactic mammography or ultrasound image guidance means can be used to identify the area of concern. Typically, more than one, for example three to five, separate core needle insertions are performed to obtain a sufficient amount of breast tissue.

Like needle biopsy, vacuum biopsy also is a minimally invasive procedure which is based on insertion of a needle into a breast tissue suspected to be abnormal. However, unlike core needle insertion which involves several separate needle insertions to acquire multiple samples, the special biopsy probe used during vacuum-assisted biopsy is inserted only once into the breast through a small skin nick made in the skin of the patient's breast. Vacuum-assisted breast biopsy systems are well known to the person working in the relevant technical field and can be obtained from different manufactures (e.g. the Mammotome biopsy system available from Ethicon Endo-Surgery, Germany).

In general, the samples to be examined are obtained from a patient suffering from a proliferative breast disease. A proliferative breast disease refers to any state of the breast tissue which is associated with an abnormal and/or uncontrolled cell proliferation. In a proliferative breast disease, a tumor is formed in the breast, i.e., an abnormal mass of cells, that results from excessive cell division and performs no useful body function. Tumors are distinguished in benign tumors and malignant tumors. Accordingly, the proliferative breast disease which leads to tumor formation may be a benign or a malignant disease.

Malignant tumors are generally cancerous which means that the patient is afflicted with breast cancer. Cancer has the potential to invade and destroy neighboring tissues and create metastases. The main types of breast cancer are invasive ductal carcinoma, invasive lobular carcinoma, papillary carcinoma, mucinous carcinoma, medullary carcinoma and tubular carcinoma. The diagnosis and classification of cancers is well known in the art and discussed in numerous publications (see, for example, Tavassoli, F. A., et al. (2003), World Health Organization: Tumours of the Breast and Female Genital Organs, WHO/IARC Classification of Tumours). According to one particular aspect of the invention, the proliferative breast disease which leads to the formation of a tumor is breast cancer.

Benign tumors are characterized in that they do not invade neighboring tissues and do not spread metastases. Normally, benign tumors do not recur after surgical removal of the tumor tissue. As used herein, benign tumors result from non-cancerous proliferative breast diseases. Such non-invasive diseases also comprise pre-cancerous conditions which are known to frequently result in a cancerous disease at a later stage. According to a further aspect of the invention, the proliferative breast disease is selected from the group of benign diseases consisting of ductal hyperplasia, preferably atypical ductal hyperplasia, papillomas, preferably ductal papillomas, sclerosing adenosis, mastopathy, Phylloides tumor, fibroadenoma, ductal carcinoma in situ (DCIS), lobular carcinoma in situ (LCIS), and apocrine metaplasia. These conditions are known in the field of medicine and are moreover described in detail in standard textbook and numerous publications (see, for example, Tavassoli, F. A., et al. (2003), World Health Organization: Tumours of the Breast and Female Genital Organs, WHO/IARC Classification of Tumours).

A ductal carcinoma in situ (DCIS) is an early form of breast cancer, which is sometimes referred to as pre-cancerous, intraductal or non-invasive cancer. In DCIS, cell proliferation has occurred inside the milk ducts and the cells have not (yet) developed the ability to spread through the breast or outside the breast. There are numerous different types of DCIS, including the comedo type of DCIS that is characterized by necrotic cells inside the breast ducts, and the non-comedo types that are further classified according to the growth pattern of tumor cells inside the ducts into solid DCIS, cribriform DCIS, and others (Tavassoli, F. A., et al. (2003), World Health Organization: Tumours of the Breast and Female Genital Organs, WHO/IARC Classification of Tumours). Normally, if DCIS is not properly treated, the cells may eventually develop the ability to spread from the ducts into the surrounding breast tissue and become cancerous.

A lobular carcinoma in situ (LCIS) refers to a proliferation of lobules cells, i.e. cells of the milk-producing glands in the back of the breasts located at the end of the ducts. LCIS is also considered as a pre-malignant tissue state and has been linked to a slightly increased risk of developing breast cancer in the future. Like DCIS, LCIS is a non-invasive cell proliferation which means that it has not yet spread into the surrounding tissues. In most cases of LCIS, the patient will never develop invasive cancer.

The term mastopathy describes various types of proliferative diseases of the breast. According to the definition published by WHO (1984), mastopathy is the fibrocystic disease (FCD) of the breast which is characterized by a disbalance between epithelial and connective tissue growth with high proliferative and regressive changes of the breast tissue.

Sclerosing adenosis (also designated adenofibrosis, fibrosing adenosis) is a benign condition whereby extra tissue grows within the breast lobules. It frequently causes breast pain. Usually the changes are microscopic, but adenosis can produce lumps, and it can show up on a mammogram, often as calcifications.

Hyperplasia is a benign breast condition caused by increased growth in the size and number of normal cells within a part of the breast. It can occur in the ducts (ductal hyperplasia) or the lobes (lobular hyperplasia). Hyperplasia may occur as atypical ductal hyperplasia or atypical lobular hyperplasia. A diagnosis of atypical ductal hyperplasia or atypical lobular hyperplasia means that the cells have developed an unusual pattern (see Tavassoli, F. A., et al. (2003), World Health Organization: Tumours of the Breast and Female Genital Organs, WHO/IARC Classification of Tumours). An apocrine metaplasia is a benign breast condition occurring in patients with fibrocystic disease.

An intraductal papilloma is a benign wart-like lump that forms within a duct just behind the areola. Intraductal papillomas can be in both breasts at the same time and are sometimes discovered following breast surgery. Women reaching the menopause are more likely to have a single intraductal papilloma, while younger women often have more than one. Papillomatosis describes multiple papillary lesions within the breast ducts.

Benign phylloides tumors are a rare type of breast lump that are most commonly found in pre-menopausal women between the ages of 40 and 50. Although unusual, a benign phyllodes tumor recurs after it has been removed, and may (rarely) develop into a borderline malignant or malignant form.

Fibroadenomas are the most common benign tumors of the female breast. They usually comprise of connective tissue, inter alia from encapsulated gland tissue. They develop at any age but are more common in young women, often teenagers, and are mistaken for cancer. They may be excised but frequently recur.

According to the invention, it was found that individuals with a proliferative breast disease associated with a tumor having an amplified ESR1 gene in the genome of the tumor cells are particularly suitable for anti-estrogen therapy, for example, by administration of Tamoxifen. The tumors of these patients have shown to be particularly responsive to anti-estrogen therapy. For the purpose of the present invention, "responsive" in the context with a tumor or a patient means that a beneficial clinical reaction to the particular applied treatment is obtained, which leads to an improvement of the disease state with respect to said tumor or said patient. Preferably, the beneficial clinical reaction is stronger when compared to tumors of patients without ESR1 amplification (for example, ER-positive lacking amplification of the ESR1 gene or ER-negative) being subjected to the same treatment.

In relation to a tumor, the beneficial clinical reaction may comprise reduction of the tumor size, stabilization of the tumor size by slowing of growth and/or reduction of the tendency to spread metastases (in case of a malignant tumor).

Preferably, a tumor which is responsive to anti-estrogen treatment will be reduced in size during or subsequent to therapy. In relation to a particular patient with a non-cancerous proliferative breast disease, the clinical reaction may also comprise the reduction of the risk of developing breast cancer. In relation to a particular patient with breast cancer the clinical reaction may also comprise delay or slowing of the disease progression, and in particular prolonging survival of the patient as compared to survival if not receiving any treatment. A patient who is responsive to anti-estrogen treatment as described above is considered suitable for anti-estrogen treatment.

An "anti-estrogen treatment" or "anti-estrogen therapy" means any measure that targets to interfere with the naturally occurring interaction between estrogen (estradiol, estriol and estrone, and preferably estradiol 17-beta) and the estrogen receptor, preferably the alpha isoform of the estrogen receptor. Specifically, anti-estrogen treatment or anti-estrogen therapy comprises measures which result in blocking the signal-transducing function of the estrogen receptor, which effects the estrogen-induced reactions, such as cell proliferation. Such measures comprise, for example, the administration of active agents or drugs that act by competitive inhibition of estrogen binding to an estrogen receptor, preferably the alpha isoform of the receptor. When administered in an therapeutically effective amount, these agents or drugs bind to the estrogen receptor, preferably the alpha isoform of the receptor, thereby blocking estrogen from binding to this receptor. According to the present invention, these compounds are referred to as "estrogen antagonists" (see below). Aside from estrogen antagonists, other current anti-estrogen strategies include destabilization and degradation of an estrogen receptor, preferably the alpha isoform, by administering a therapeutically effective amount of a selective estrogen receptor downregulator (e.g. Fulvestrant) or disruption of estrogen synthesis by administering a therapeutically effective amount of an aromatase inhibitor (e.g. Anastozole, Exemestan).

The term "therapeutically effective amount" refers to an amount of a drug effective to treat a disease or disorder in a mammal, preferably a human. In the case of a cancerous or non-cancerous proliferative breast disease, a therapeutically effective amount of a drug normally inhibits (i.e. slows to some extent and preferably stops) tumor growth and/or reduces tumor size. In the case of breast cancer, it may also inhibit (i.e. slow to some extent and preferably stop) cancer cell infiltration into peripheral organs and inhibit (i.e. slow to some extent and preferably stop) the development of tumor metastases. Furthermore, it may kill existing breast cancer cells. A therapeutically effective amount of a drug may also relieve one or more of the symptoms associated with a proliferative breast disease, such as breast cancer. For therapy, efficacy of the drug administration can be measured, for example, by assessing the time to disease progression (TTP) and/or determining the response rate (RR). Methods for determining the efficacy of therapy are dependent on the particular disorder and moreover well-known to the person skilled in the art (Kelloff G. F. et al. (2005) Eur J Cancer 41: 491-501). The optimum dose and treatment regimen for the particular agent administered as an anti-estrogen therapeutic are described in detail in the state of the art for several anti-estrogen drugs. For example, with respect to Tamoxifen, a therapeutically effective dosis may be about 10, 20, 30, 40, 50, 60, 70, 80, 90 and 100 mg/per day for a period of one to several years for example 2-5 years. A dosis of 60 mg/per day for a period of 5 years is reported in the literature (Kung et al. (2003), J Clin Endocrinol Metab, 88(7):3130).

According to a preferred embodiment of the invention, the anti-estrogen treatment mentioned in the above methods comprises administration of an estrogen antagonist. According to the present invention, the term "estrogen antagonist" refers to a compound that binds to an estrogen receptor, and preferably to the alpha isoform of the estrogen receptor, (either in homodimeric or heterodimeric form), thereby inhibiting or substantially reducing the effect of the respective agonist (estrogen). The estrogen antagonist can be a competitive or non-competitive antagonist. A competitive estrogen antagonist competes with estrogen (or other agonists) for an estrogen receptor. By binding of the competitive estrogen antagonist to an estrogen receptor, the agonist estrogen is blocked from binding to the receptor. An example for such a competitive estrogen antagonist is Tamoxifen. In comparison, non-competitive antagonists antagonize the estrogen receptors by other means. For example, trilostane (Modrenal, Bioenvision) binds to the AF-1 domain of ER-alpha and ER-beta receptors in a non-competitive manner which is presumed to be allosteric. The AF-1 domain is involved in protein-protein interactions (but not estrogen binding) and trilostane binding thus contributes to modulation of receptor dimerization which is a prerequisite for activation (Puddlefoot J. R. et al. (2002), Int J Cancer 101: 17-22). Competitive or non-competitive estrogen antagonists can be found by common estrogen receptor binding assays, such as those described in the National Institutes of Health (NIH) publication no. 03-4504 (2002) including the protocols provided in the appendix.

According to a particularly preferred embodiment of the invention, the estrogen antagonist is selected from the group consisting of Tamoxifen (purchasable e.g. as Novaldex from Astra Zeneca, or from other manufactures, for example under the trade names Jenoxifen, Kessar, Nourytam, Tamobeta, Tamofen, Tamokadin, Tamoxasta, Tamox-GRY, Tamoxifen AL, Tamoxifen-biosyn, Tamoxifen cell pharm, Tamoxifen Heumann, Tamoxifen Hexal, Tamoxifen medac, Tamoxifen-ratiopharm, Tamoxigenat, Tamoximerck, Tamoxistad, Zemide, and the like), Raloxifene (purchasable e.g. as Revista from Eli Lilly), Clomifene (purchasable e.g. as Clomhexal from Hexal), Toremifene (purchasable as Fareston from GTx Inc.), Trilostane (purchasable as Modrenal from Bioenvision, UK only) or functional derivatives thereof. According to a particularly preferred embodiment of the invention, the estrogen antagonist is Tamoxifen or a functional derivative thereof. Functional derivates are generally obtained from the above compounds by chemical modification. In the case of Tamoxifen, such derivates comprise for example 4-hydroxytamoxifen and 4-hydroxy-N-desmethyl-tamoxifen (Endoxifen).

Alternatively, the anti-estrogen treatment may comprise the administration of an agent which interferes with estrogen synthesis. By inhibiting, blocking or reducing the production of estrogens, a decrease in binding of estrogen (such as estradiol) to the estrogen receptors, preferably the estrogen receptor alpha, can be achieved. Agents which interfere with estrogen synthesis comprise, for example, aromatase inhibitors. Aromatases belong to the group of enzymes which comprise cytochrome P450 and catalyze the aromatization of androgens to estrogens, a key step in the production of estrogens. The inhibition of the aromatase enzyme results in reduced estrogen levels (hypoestrogenism). Aromatase inhibitors comprise compounds such as Anastrozole (purchasable as Arimidex from Astra Zeneca), Letrozole (purchasable as Femara from Novartis Pharmaceuticals), Formestan (purchasable as Lentaron from Novartis) and Exemestane (purchasable as Aromasin from Pharmacia). Aromatase inhibitors may be identified by common enzyme inhibition assay using the aromatase enzyme. As an example such an assay is described in Matsui et al (2005), J Pharm Biomed Anal, 38(2):307-12.

According to another aspect, the anti-estrogen treatment comprises administration of an agent which downregulates expression of an estrogen receptor, preferably the estrogen receptor alpha. Preferably, the agent which downregulates expression of an estrogen receptor is Fulvestrant or a functional derivative thereof. Fulvestrant may be obtained under the name Faslodex from Astra Zeneca. Fulvestrant is an estrogen receptor antagonist which blocks estrogen binding to an estrogen receptor, preferably to the estrogen receptor alpha. Additionally, it induces downregulation of the receptor (Morris, C. and Wakeling, A., Endocr Relat Cancer (2002), 9(4): 267-76; Gradishar, W. J., Oncologist. (2004), 9(4): 378-84). Other compounds to trigger downregulation of the estrogen receptor may include small interfering RNAs (siRNAs), targeting specific (e.g. ER) mRNA (see Grunweller et al. (2005), Current Medicinal Chemistry 12(26), 3143-3161), or other modifiers of transcription as reviewed in Melnick et al. (2005), JCO 23(17), 3957-3970).

The anti-estrogen treatment may be performed as a monotherapy or in a combination therapy together with chemotherapy and/or radiation. Preferably, the anti-estrogen treatments are to be performed as a monotherapy. Anti-estrogen therapy may also be performed as an adjuvant therapy in patients afflicted with breast cancer in order to prevent metastases. Anti-estrogen therapy can also be useful for prophylactic treatment of patients at high risk of developing breast cancer in order to prevent cancer development.

Normally, tumors of the breast, such as carcinomas, are removed by surgical means in a first therapeutic step which is followed most cases by an adjuvant therapy. At present, several surgical approaches have been established, including lumpectomy with and without subsequent radiation therapy and modified radical mastectomy. A lumpectomy is the removal of the primary breast tumor and a small amount of surrounding tissue. Usually, most of the axillary lymph nodes are also removed. A modified radical mastectomy is the removal of the whole breast, most of the axillary lymph nodes, and often the lining over the chest muscles. The smaller of the two chest muscles is sometimes taken out to help in removing the lymph nodes. Where surgical removal of the tumor is not possible, for example in cases where invasion of the healthy tissue is in a too advanced state, chemotherapy is often employed to reduce the tumor size before lumpectomy.

The principal purpose of adjuvant therapy is to eradicate cancer cells that may have spread from the tumor located in the breast and remain after surgical removal. Thus, treatment is normally performed systemic, for example, by oral uptake or injection into the bloodstream which allows the agent to circulate through the body. Whether a patient has to be treated with an adjuvant therapy is dependent on the individual risk of the patient to develop metastases at a later stage of the disease and several other factors, such as tumor size, histological type of the tumor as well as the grade of aggressiveness of the disease. On the basis of these factors, patients are attributed to a low, mid or high risk to develop metastases. Most frequently, adjuvant therapy for breast cancer comprises anti-estrogen therapy or chemotherapy, either alone or in combination.

In the context of an adjuvant therapy, chemotherapy is commonly performed in accordance with the so-called CNF scheme, using the substances cyclophosphomid, metotrexat and 5-fluoruracil. Alternatively, chemotherapeutic regimens based on anthracycline-containing agents are also available. Other frequently used chemotherapeutic agents include alkylating agents, e.g. ethylenimines and methylamelamines, such as thiotepa, altretamine, triethylenemelamine, trietylenephosphoramide, triethylenethiophosphaoramide and trimethylolomelamine; alkyl sulfonates such as busulfan and piposulfan; nitrogen mustards such as ifosfamide, chlorambucil, estramustine, chlornaphazine, cholophosphamide, mechlorethamine, mechlorethamine oxide hydrochlonde, novembichin, phenesterine, prednimustine, trofosfamide; nitrosureas such as fotemustine, lomustine, carmustine, chlorozotocin, nimustine, ranimustine; aziridines such as carboquone, benzodopa, meturedopa, uredopa; purine analogs such as 6-mercaptopurine, fludarabine, thioguanine; pyrimidine analogs such as ancitabine, azacitidine, 6-azauridine, carmofur, cytarabine, dideoxyuridine, doxifluridine, enocitabine, floxuridine, 5-FU; and nitrosureas such as carmustine, chlorozotocin, fotemustine, lomustine, nimustine, ranimustine and the like.

However, due to the mainly unspecific mode of action of the respective agents, chemotherapy is a severe treatment with considerable side effects for the patient. Thus, it is highly desirable to identify patients which can effectively treated without or with low-dose chemotherapy. In this context, it is of critical relevance to identify patients which exhibit an enhanced clinical response to anti-estrogen therapy, such as administration of Tamoxifen. Thus, in one aspect the present invention provides a suitable means for identifying a subgroup of estrogen receptor-positive patients which show an enhanced response to anti-estrogen treatment and, therefore, are suitable to be subjected to treatment protocols which are based on the administration of anti-estrogens, either without the need for concurrent chemotherapy or in combination with low-dose chemotherapy. Therefore, the invention contributes to a better prognosis as well as to an improved overall condition of the patient during treatment. In this manner, effective treatment can be conducted in a way that is much less associated with the unpleasant and health-threatening effects of chemotherapy and at the same time maintain a high level of medical effect.

The invention also provides a suitable method for the long-term surveillance of the responsiveness of a tumor or patient to anti-estrogen treatment, in which the method for identifying a tumor as responsive to anti-estrogen treatment as described herein is performed sequentially, for example, twice within a period of 3, 6, 9, 12 or 18 month in order to monitor if changes to the amplification status have occured during a particular treatment regimen, for example treatment with Tamoxifen or another anti-estrogen drug. The method will be particularly suitable to evaluate whether a given tumor resulting from a proliferative breast disease develops resistance against the anti-estrogen treatment.

Tumors cells with low level amplification, with normal ESR1 gene copy numbers, or cells with a loss of ESR1 might not respond optimal to anti-estrogen treatment or even escape such treatment. Such cells are likely to have a selection advantage under anti-estrogen treatment and might be a source for the development of hormone refractory (resistant) tumors. Such an effect is known for topoisomerase 2 alpha, the molecular target of anthracycline therapy. Studies carried out in vitro suggested that cell lines without TOP2A aberrations or those with TOP2A deletion are less sensitive to anthracycline therapy than cell lines with TOP2A amplification or overexpression (Järvinen et al. (2000), Am J Pathol 156:839). Only recently, this observation has been confirmed in a clinical study including 391 breast cancer patients (Scandinavian Breast Group Trial 9401 (2006), J Clin Oncol.

24(16):2428). Accordingly, monitoring of changes in the ESR1 amplification status in sequential biopsies from breast cancer patients could be a potential marker for prediction of response to anti-estrogen treatment.

The methods of the present invention are based on the predictive impact of ESR1 gene amplification. ESR1 amplification can be conveniently detected by means which directly target the ESR1 coding sequence provided by nucleotides 1048135 to 1343855 in SEQ ID NO:1 or at least a part of this coding sequence. Furthermore, ESR1 amplification can also be confirmed by detecting amplification of a sequence portion of SEQ ID NO:1 which is located outside of the ESR1 coding sequence. Several polymorphisms exist in the human sequence of the ESR1 gene. Moreover, non-coding regions within the ESR1 gene might deviate to some extent between distinct individuals. Thus, although the present invention mainly refers to nucleotide sequence portions of SEQ ID NO:1 as a reference, it is clear that also nucleotide sequences having substantial sequence identity to nucleotide sequence portions of SEQ ID NO:1 may be equally used in the context of the invention. Preferably, such nucleotide sequence shares at least 70, 75, 80, 85, 90, 91, 92, 93, 94, 95, 96, 97, 98, 99 or even 99.5 % sequence identity to a nucleotide sequence portion of SEQ ID NO:1. Preferably, such nucleotide sequence shares at least 95% sequence identity to a nucleotide sequence portion of SEQ ID NO:1.

Generally, the amplification of a specific gene leads to the co-amplification of genomic sequences which are located 5' or 3' of said gene. Hence, the chromosomal fragment which is duplicated during amplification regularly not only comprises the sequence of a single gene, but also additional genomic sequences which can be used as a marker to confirm ESR1 amplification. As described in example 6, a sequence range having a size of approximately 2.7 Mb (provided in SEQ ID NO:1) which contains the ESR1 coding sequence was found to be suitable for confirming amplification of the ESR1 coding sequence. Specifically, it was found that the sequences of SEQ ID NO:1 which are located outside the ESR1 coding sequence are only amplified, if the ESR1 coding sequence is also amplified, i.e. they are co-amplified with the ESR1 coding sequence. This means that in cases where amplification of a sequence portion of SEQ ID NO:1 (or a related nucleotide sequence having, for example, at least 95% sequence identity to such portion) is detected, for example, amplification of a sequence located at the very 5' or 3' end of the sequence of SEQ ID NO:1, amplification of ESR1 is to be assumed. Thus, ESR1 amplification can be confirmed by detecting amplification of any sequence portion of SEQ ID NO:1 (or a nucleotide sequence having, for example, at least 95% sequence identity to such portion) which is either located inside or outside of the ESR1 coding sequence.

A nucleotide sequence portion located outside the ESR1 coding sequence which can be selected for confirming ESR1 amplification may be located in the region extending from position 1 to position 1048135 of the sequence shown in SEQ ID NO:1. For example, the nucleotide sequence portion may be located between nucleotides 100000 to 1048135, 200000 to 1048135, 300000 to 1048135, 400000 to 1048135, 500000 to 1048135, 600000 to 1048135, 700000 to 1048135, 750000 to 1048135, 760000 to 1048135, 770000 to 1048135, 780000 to 1048135, 790000 to 1048135, 800000 to 1048135, 810000 to 1048135, 820000 to 1048135, 830000 to 1048135, 840000 to 1048135, 850000 to 1048135, 860000 to 1048135, 870000 to 1048135, 880000 to 1048135, 890000 to 1048135, 900000 to 1048135, 910000 to 1048135, 920000 to 1048135, 930000 to 1048135, 940000 to 1048135, 950000 to 1048135, 960000 to 1048135, 970000 to 1048135, 980000 to 1048135, 990000 to 1048135, 1000000 to 1048135, and even more preferably between 1010000 to 1048135, 1020000 to 1048135, 1030000 to 1048135, 1040000 to 1048135, 1041000 to 1048135, 1042000 to 1048135, 1043000 to 1048135, 1044000 to 1048135, 1045000 to 1048135, 1046000 to 1048135, 1047000 to 1048135, 1048000 to 1048135 of the sequence shown in SEQ ID NO: 1. Likewise, the nucleotide sequence portion may be located between nucleotides within the region extending from position 1343855 to 2725892 of the sequence shown in SEQ ID NO: 1. For example, the nucleotide sequence portion may be located between nucleotides 1343855 to 1344000, 1343855 to 1345000, 1343855 to 1346000, 1343855 to 1347000, 1343855 to 1348000, 1343855 to 1349000, 1343855 to 1350000, 1343855 to 1351000, 1343855 to 1352000, 1343855 to 1353000, 1343855 to 1354000, 1343855 to 1355000, 1343855 to 1356000, 1343855 to 1357000, 1343855 to 1358000, 1343855 to 1359000, 1343855 to 1360000, 1343855 to 1370000, 1343855 to 1380000, 1343855 to 1390000, 1343855 to 1400000, 1343855 to 1410000, 1343855 to 1420000, 1343855 to 1430000, 1343855 to 1440000, 1343855 to 1450000, 1343855 to 1460000, 1343855 to 1470000, 1343855 to 1480000, 1343855 to 1490000, 1343855 to 1500000, 1343855 to 1510000, 1343855 to 1520000, 1343855 to 1530000, 1343855 to 1540000, 1343855 to 1550000, 1343855 to 1560000, 1343855 to 1570000, 1343855 to 1580000, 1343855 to 1590000, 1343855 to 1600000, 1343855 to 1610000, 1343855 to 1620000, 1343855 to 1630000, 1343855 to 1640000, 1343855 to 1650000, 1343855 to 1660000, 1343855 to 1670000, 1343855 to 1680000, 1343855 to 1690000, 1343855 to 1700000, 1343855 to 1800000, 1343855 to 1900000, 1343855 to 2000000, 1343855 to 2100000, 1343855 to 2200000, 1343855 to 2300000, 1343855 to 2400000, 1343855 to 2500000 or 1343855 to 2725892 of the sequence shown in SEQ ID NO: 1. Of course, it is also possible that the nucleotide sequence portion covers a part of the ESR1 coding sequence and extends into the flanking region framing ESR1.

If amplification of ESR1 is tested by detecting amplification of a sequence portion of SEQ ID NO:1 which is located outside of the ESR1 coding sequence (or a nucleotide sequence having, for example, at least 95% sequence identity to such portion) and no amplification of the selected sequence portion can be detected in a sample, this does not necessarily allows the conclusion that no ESR1 amplification is present in the tested cells. In these cases, the amplicon (i.e. the amplified genomic sequence entity consisting of the ESR1 gene and flanking regions) in the chromosome might be smaller in size, so that further detection assays using nucleotide sequence portions of SEQ ID NO:1 (or nucleotide sequences having, for example, at least 95% sequence identity to such portions) which are in closer vicinity to the ESR1 gene or which are directly derived from the ESR1 gene should be performed. The person of skill will have no problems to determine flanking regions on the 5' end and at the 3' end of the ESR1 gene, respectively, which are obligatory co-amplified in each ESR1 amplification event. Thus, a "minimum" amplicon can be readily determined by the person skilled in the art, simply by screening a high number of tumor cell samples for ESR1 amplification, for example by FISH using a probe which directly binds to the ESR1 coding sequence, and subsequently determining the 5' and 3' ends of the Identified amplicons. Once in receipt of such minimum amplicon, it is possible not only to positively confirm an ESR1 amplification on the basis of an amplified sequences outside the coding sequence, but also to exclude ESR1 amplification on the basis of such sequences in case the test result should be negative. In a method using the minimum amplicon, essentially all tumor cells which exhibit ESR1 amplification will be identified. Thus, according to a preferred aspect, a nucleotide sequence portion of the nucleotide sequence of SEQ ID NO:1 (or a nucleotide sequence having, for example, at least 95% sequence identity to such portion) for use in the detecting step is chosen which is obligatory co-amplified with the ESR1 coding sequence.

An alternative possibility to establish a method which identifies all ESR1-amplified tumor cells is to select the ESR1 coding sequence for amplification analysis. Thus, according to a preferred embodiment of the invention, the nucleotide sequence portion of SEQ ID NO:1 comprises at least a part of the ESR1 coding sequence ranging from nucleotide positions 1048135 to 1343855 of SEQ ID NO:1. Alternatively, a nucleotide sequence having the above described sequence identity to such portion, preferably at least 95%, may also be used. According to this particular embodiment, amplification of at least a part of the ESR1 gene is directly tested. The sequence portion can be selected to include a part of the coding sequence of ESR1 and a part of the flanking regions from the 3' or 5' end of the ESR1 coding sequence. The selected nucleotide sequence portion of SEQ ID NO:1 may also comprise the complete ESR1 coding sequence, as provided by nucleotide positions 1048135 to 1343855 of SEQ ID NO:1, for example, as a probe to be used in FISH assays. According to a further preferred embodiment of the invention, the nucleotide sequence portion of SEQ ID NO:1 is located within the ESR1 coding sequence ranging from nucleotide positions 1048135 to 1343855 of SEQ ID NO:1. Again, nucleotide sequence having, for example, at least 95% sequence identity to such portions are also included according to the invention.

All methods of the present invention comprise the step of detecting in a cell sample from a tumor whether a nucleotide sequence portion of the nucleotide sequence of SEQ ID NO:1, for example the ESR1 coding sequence, or a nucleotide sequence having, for example, at least 95% sequence identity to such nucleotide sequence portion is amplified in the genome of the tumor cells. As used herein, a "nucleotide sequence portion of SEQ ID NO:1" means a segment of the genomic DNA as depicted in SEQ ID NO:1 consisting of at least 10 contiguous nucleotides, preferably of at least 20, 30, 40, 50 or 100 nucleotides, and most preferably of at least 50000, 100000, 150000 or more nucleotides of the sequence of SEQ ID NO:1. The size of the nucleotide sequence portion used for detecting amplification will depend on the method of detection of said sequence portion (see below). For example, if FISH assays are used for amplification detection, the selected sequence portion will correspond to the length of the probe and will preferably have a size of several kilobases, for example 40, 50, 60, 70, 80 100, 120, 140, 160, 180, 200, 300 or 400 kilobases. In comparison, if amplification detection will be performed by PCR, the sequence portion will correspond to the size the PCR product obtained by using specific primers, for example 50, 100, 150, 200, 300, 400 or 500 nucleotides. If amplification detection is performed by Southern Blotting, the nucleotide sequence portion to be selected can be in the range of 30, 40, 50, 60 nucleotides which corresponds to a common DNA probe regularly used in Southern Blotting.

An identity of 95% means that when aligning corresponding nucleotide sequences (whereas the use of gaps is allowed for proper alignment of corresponding nucleotides) only 5 nucleotides over a length of 100 nucleotides should be different. Preferably, nucleotide sequence portions having a size sufficiently large to exclude false-positive detection of amplification, for example by unspecific hybridization, are used.

As used herein, detecting whether a selected nucleotide sequence portion of the nucleotide sequence of SEQ ID NO:1 or a nucleotide sequence having substantial sequence identity thereto is amplified means that it is examined whether the nucleotide sequence portion of SEQ ID NO:1 or a nucleotide sequence having substantial sequence identity to such portion occurs in an increased copy number in the genome of a tested tumor cell relative to the genome of a normal cell with a balanced caryotype, preferably a normal diploid somatic cell of the same individual. Diploid organisms, such as mammals, usually have two copies (allels) of a given genomic nucleotide sequence, such as a gene sequence, in their somatic cells. Hence, a balanced caryotype of a somatic mammalian cell regularly comprises two copies of a given nucleotide sequence, for example of the ESR1 gene.

If the nucleotide sequence portion of SEQ ID NO:1 or a nucleotide sequence having, for example, at least 95% sequence identity to such portion is amplified in the cell sample, more copies of said nucleotide sequence portion or its related sequence are present in the genome of a tested cell when compared to a normal cell with a balanced caryotype. Thus, in cases where the selected nucleotide sequence portion is amplified in the genome of a cell, the copy number of said nucleotide sequence portion exceeds 2. For example, the copy number of said nucleotide sequence portion may be 3, 4, 5, 6, 7, 8, 9, 10, 11, 12, 13, 14, 15, 20, 30, 40, 50 or even up to 100 copies per cell. The copy number of said nucleotide sequence portion can also be decreased relative to the balanced caryotype of a somatic mammalian cell, which means that the cells have lost one or both copies of the nucleotide sequence portion from the relevant chromosome, for example from human chromosome 6. In cases where the nucleotide sequence portion has not been amplified, 2 copies of said sequence should be present per cell.

Typically, amplification of a gene, a gene fragment, or a larger portion of a chromosome comprising more than one gene is determined by assessing the number or intensities of signals obtained (depending on the specific detection method) for the gene, fragment or portion of interest relative to the number or intensities of signals of a reference sequence from the same DNA sample. For example, a sequence for which the copy number is known (i.e. from a gene or a non-coding DNA stretch which does not undergo amplification events) may be used as a reference. The nature of the reference sequence will depend on the specific method of determining the amplification event, e.g. PCR, Southern-Blot, FISH and the like (see below). For example, in fluorescence in situ hybridization assays, the sequence of the centromere of human chromosome 6 or 17 might be conveniently used as an intrinsic reference. Alternatively, if PCR approaches are used for assessing the copy number, reference genes may comprise one or more of the genes commonly used as "housekeeping genes" such as genes encoding human albumin glyceraldehyde 3-phosphate dehydrogenase (GAPDH), (β-actin, β-2 microglobulin, hydroxymethylbilane synthase, hypoxanthine phosphoribosylm transferase I, ribosomal protein L13a, succinate dehydrogenase complex (subunit A), TATA box binding protein, ubiquitin C, β-Globin (HBB), Phosphoglycerate kinase 1 (PGK1), Ribosomal protein L4 (RPL4), Large ribosomal protein P0 (RPLP0), Eukaryotic elongation factor 1 (EEF1A1), Eukaryotic translation elongation factor 1 (EEF1G), Succinate dehydrogenase complex A (SDHA), Muscleblind-like 2 (MBNL2), 28S Ribosomal RNA (28S), 18S Ribosomal RNA (18S), and the like. In cases, where an internal reference is simultaneously tested with the cells or DNA of the test samples, e.g. a normal somatic cell with a balanced caryotype, it may not be necessary to determine the specific number of copies of the ESR1 gene as long as it is shown that significantly more detection signals (which are correlated to the copy number of the ESR1 gene) are obtained in the test sample relative to the control sample.

The amplification of the nucleotide sequence portion of SEQ ID NO:1 (or the nucleotide sequence having, for example, at least 95% sequence identity to such portion) can be detected according to methods well-known in the art. The amplification is generally determined by analysis of the genomic DNA of a cell sample. The genomic DNA may be isolated and/or purified before determining the amplification status as usually required for PCR-based methods. For purification, commercially available kits, such as the QIAgen Genomic tip system (QIAgen, Hilden, Germany), may be employed. Other methods for purifying genomic DNA from different, types of cells, such as cells from human tissues are discussed in Sambrook, J. et al. (2001); Molecular Cloning: A Laboratory Manual (Third Edition), Cold Spring Harbor Laboratory Press. On the other hand, if cytogenic methods like fluorescence in situ hybridization (FISH) or immunohistochemistry are used, complete cells or tissue portions may be employed without the need to isolate the DNA in an initial step.

Several methods of identifying gene amplification events and/or determining the copy number of a DNA entity (such as a gene) have been described in the art. According to the present invention, detecting whether said nucleotide sequence portion of SEQ ID NO:1 (or a nucleotide sequence having, for example, at least 95% sequence identity to such portion) is amplified comprises DNA analysis using a probe which hybridizes to said nucleotide sequence portion (or to a nucleotide sequence having, for example, at least 95% sequence identity to such portion). Most preferably, the probe hybridizes to the ESR1 coding sequence ranging from nucleotide positions 1048135 to 1343855 of SEQ ID NO:1 or a part thereof (or to a nucleotide sequence having, for example, at least 95% sequence identity to such portion). As used herein, "hybridization" in the context with a primer or probe means that the primer or probe forms a non-covalent interaction with the target polynucleotide, e.g. the ESR1 gene in the genomic DNA of the cell to be tested or a flanking region thereto which is located on the same amplicon like the ESR1 gene. Preferably, the hybridization is a specific hybridization. As used herein, a specific hybridization of a probe or primer means that the probe or primer substantially only hybridizes with the target DNA sequence to which it shows complementarity and substantially not to unrelated sequences. Specific hybridization of a probe or primer occurs when the level of sequence identity between the probe or primer and the target sequence is sufficiently high. Generally, nucleotide sequences which share about 50, 60, 70 or 80%, more preferably 90 or 95, 96, 97, 98, or 99% sequence identity will specifically hybridize.

A specifically hybridized probe or primer remains hybridized to its target sequence under stringent conditions. As used herein, "stringent conditions" are conditions of temperature and salt that lead to an environment in which substantially only allows a primer or probe to remain hybridized to the target sequence in the case of a substantial sequence identity between the probe or primer and the target sequence. Stringent conditions are sequence dependent and are different under environmental parameters. Generally, stringent conditions are selected to be about 5° C. to 20° C. lower than the thermal melting point for the specific sequence at a defined ionic strength and pH. The thermal melting point is the temperature (under defined ionic strength and pH) at which 50% of the target sequence hybridizes to a perfectly matched (i.e. perfectly complementary) probe. For example, stringent conditions may include hybridization at a temperature ranging from 42° to 65° C. The hybridization solution and washing buffers used may be of high ionic strength, for example 6 times SSC buffer with or without the addition of SDS or other detergents.

Conditions for nucleic acid hybridization and calculation of stringencies can be found in Sambrook, J. et al. (2001); Molecular Cloning: A Laboratory Manual (Third Edition), Cold Spring Harbor Laboratory Press and Haymes, B. D. et al. (1985) in Nucleic Acid Hybridization, A Practical Approach, IRL Press, Washington, D.C. Moreover, computer programs are available for assisting the constructions of optimal probes and primers, for example, InforMax by Vector NTI (distributed by Invitrogen) or Premier Biosoft by Primer Premier.

A nucleic acid probe or primer used for the detection of the amplification of a nucleotide sequence portion of SEQ ID NO:1 or a nucleotide sequence having, for example, at least 95% sequence identity to such portion may be a perfect complement of the selected sequence portion or a part thereof (e.g. a sequence within the ESR1 coding sequence or a sequence located in a genomic region flanking ESR1) or may be substantially complementary thereto. A "perfect" complementary probe or primer means that every nucleotide of the probe or primer molecule is complementary to the nucleotide at the corresponding position of the target sequence. A probe or primer is "substantially complementary" to a target sequence if one or more nucleotides in the primer or probe are not complementary to the corresponding nucleotide in the target sequence, whereas a sufficient number of complementary nucleotides exist, so that the specific hybridization can occur.

Specific hybridization of a probe to the corresponding nucleotide sequence portion enables detection of the number of copies of said nucleotide sequence portion in a sample, such as a tissue sample. For this purpose, the probe will comprise a detectable label. Numerous different substances are available in the art for labeling a DNA probe, including compounds or composition detectable by spectroscopic, photochemical, biochemical, immunochemical, electrical, optical or chemical means. The labeling is intended to encompass direct labeling of the probe by coupling (i.e., physically linking) a detectable substance to the probe, as well as indirect labeling of the probe by reactivity with another reagent that is directly labeled. Examples of indirect labeling include end-labeling of a DNA probe with biotin such that it can be detected with fluorescently labeled streptavidin. Alternatively, the probes may be labeled with digoxigenin which can be detected with an anti-digoxigenin antibody which in turn can be labeled or recognized by a labeled secondary antibody. Detectable labels for use in the present invention include magnetic beads (e.g., Dynabeads), fluorescent dyes (such as fluorescein, texas red, rhodamine, CY3, CY5, Alexa dyes, green fluorescent protein, and others), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Numerous other systems and compound s for labeling DNA probes are known in the art.

According to the invention, detecting whether the nucleotide sequence portion of SEQ ID NO:1, for example a sequence located within the coding sequence of ESR1, or a nucleotide sequence having, for example, at least 95% sequence identity to such portion is amplified may comprise Southern-Blotting. Southern blotting is a well established method for locating a particular DNA sequence within a complex mixture. DNA, such as genomic DNA, is digested with a restriction enzyme and separated by gel electrophoresis in an agarose gel. Subsequently, the DNA is transferred from the agarose gel onto a membrane (such as a nylon or nitrocellulose membrane) which is incubated with a labeled DNA probe specific for the sequence to be detected. The location of DNA fragments derived from the genomic DNA that hybridizes with the probe can be displayed by detecting the label. If the ESR1 gene is amplified, at least two fragments (of the same or different size) should be detected in Southern blotting. The probes used in Southern blotting are usually indirectly labeled with molecules that can be detected by systems that provide for an enhanced signal intensity (such as digoxigenin detection by an anti-digoxigenin antibody or biotin detection by horseradish peroxidase-conjugated streptavidin and subsequent exposure to a chemiluminescent substrate). Alternatively, Southern blotting probes are often radiolabled which produces a strong signal. As a consequence, probes used in Southern blotting may be of considerably short length when compared to other hybridization approaches (see below). Usually, the probe used in Southern blotting will have the size of 15-20 bp, more preferably up to 25, 30, 35, 40, 45, 50, 55, 60 or 65 bp.

According to a particularly preferred aspect, detecting whether the nucleotide sequence portion of SEQ ID NO:1, for example a sequence located within the coding sequence of ESR1, or a nucleotide sequence having, for example, at least 95% sequence identity to such portion is amplified comprises fluorescent in-situ hybridization (FISH). Protocols for conducting FISH analysis with labeled probes are available in the art (see, for example, Cherif et al. (1989) Hum Genet. 1989 March;81(4):358 or Hyytinen et al. (1994) Cytometry 16(2): 93). In such an in-situ hybridization assay, the cells or tissues to be examined are normally fixed to a solid support, such as a glass slide. Cells may be intact in case of touch preparations of surgical samples or truncated in case of tissue sections. Subsequently, the cells are typically denatured with heat or alkali. The cells are then contacted with a hybridization solution at a moderate temperature to permit annealing of labeled probes specific to the nucleic acid sequence encoding the protein. The probes are typically labeled, e.g., with one or more fluorescent reporters. The targets are then washed at a predetermined stringency or at an increasing stringency until an appropriate signal to noise ratio is obtained. When the fluorescence-labeled nucleic acid probes are hybridized to cellular DNA targets, the hybridized probes can be viewed directly using a fluorescence microscope. By using multiple nucleic acid probes with different fluorescence colors, simultaneous multicolored analysis (i.e., for different genes or sequences) can be performed in a single step on a target cell. Fluorochrome-directly labeled nucleic acid probes eliminate the need for multi-layer detection procedures (e.g., antibody-based system) which allows for fast processing and also reduces non-specific background signals. The fluorochrome-directly labeled nucleic acid probes used in FISH assays are usually longer than those used in Southern-blotting. Conventional fluorescence in situ hybridization (FISH) commonly uses cloned genomic probes for hybridization to fixed, denatured chromosomes. These genomic probes are generally large and most often cloned into vectors, such as cosmids, yeast, or bacterial artificial chromosomes that accept genomic inserts having a size of up to several 100 kilobases. According to the invention, the FISH probe may have a size of 1, 5, 10, 20, 30, 40, 50, 60 or up to 100 kb, or even of 200, 300 or 400 kb. FISH probes may be directly labeled (e.g. by fluorescent dyes) or indirectly labeled (e.g. by a hapten, such as digoxigenin or biotin). According to the invention, it is most preferred to use fluorescent labels, so that the result of the hybridization to the genomic DNA of the test sample (e.g. cells of tissue derived from biopsy) can directly be observed. As a intrinsic reference, the sequence of the centromere of human chromosome 6 or 17 might be conveniently used in FISH assays (see examples). Labeling kits for fluorescence labeling may be obtained from different manufacturers, such as the SpectrumO-range- SpectrumGreen-, and Spectrum-Red-labeling kit purchasable by Vysis Inc., Downer's Grove, Ill., USA. FISH assays have found widespread use in the detection of gene amplification events, for example in the context of detection of the erb-B2 (HER-2/neu) gene encoding the orphaned receptor tyrosine kinase Erb-B2 (also referred to as HER-2 or neu) which is reported to be a frequently amplified oncogene in breast cancer. See, for example, the publications of Masood et al. (1998), Ann Clin Lab Sci. 28(4):215, Press et al. (2002) J Clin Oncol. 2002 20(14):3095, all of which are included by reference.

A further alternative to detect a potential amplification of the nucleotide sequence portion of SEQ ID NO:1, for example a sequence located within the coding sequence of ESR1, or a nucleotide sequence having, for example, at least 95% sequence identity to such portion involves Comparative Genomic Hybridization (CHG). This cytogenetic method allows the entire genome to be scanned in a single step for copy number aberrations in chromosomal material. CGH is described in detail, for example in Kallioniemi O., et al. (1992), Science 258: 818-821 (conventional CGH) or Solinas-Toldo S., et al., (1997), Genes Chromosomes Cancer 4: 399-407 (matrix CGH). In CGH, the complete genomic DNA of a cell or cell population to be examined, such as a tumor cell (test DNA), is used as a probe in a hybridization assay, typically against the genomic DNA of normal healthy cells (reference DNA). Test and reference DNA are differently labeled and co-hybridized on a target matrix which comprises of metaphase chromosome spreads from healthy individuals (conventional CGH) or of an array of defined DNA sequences (cloned human genome fragments of several Kilobases or oligonucleotides; array- or matrix-CGH). It may also be possible to perform CGH without simultaneous co-hybridization of a reference DNA, e.g. when using so-called GeneChips (Affymetrix Santa Clara, Calif.).

Chromosomal regions which have been gained or lost when compared to the balanced caryotype control DNA can be detected by their increased or decreased staining relative to the general staining of the reference genomic DNA. Regions in an increased copy number give rise to a stronger signal compared to the control DNA. One may also, as a negative control, test a reference DNA from a healthy tissue, preferably tissue of the same part of the body (e.g. healthy breast tissue). The reference DNA may be derived from the donor of the tumor tissue or from another healthy donor. The alterations are classified as DNA gains and losses and reveal a characteristic pattern that includes copy number changes at chromosomal and subchromosomal levels. The use of CGH for analysis of solid tumors has revealed a number of recurrent chromosomes copy number aberrations including amplifications that had not been detected previously. For example, by use of CGH amplifications at chromosome 3q26-27 and 20q13 in various tumors were detected and led to the identification of target genes, such as PIK3CA and ZNF217 which are amplified in ovarian cancer and breast cancer, respectively.

As used herein, the term CGH comprises matrix CGH, array CGH and any other method of comparative genome hybridization using isolated labeled DNA and complementary DNA fixed on a solid surface. Most conveniently, CGH methods are conducted by use of array-based hybridization formats. Arrays typically comprise a multiplicity of different probe or target nucleic acids attached to one or more surfaces. Preferably, the surface is a solid surface, such as polyethylene, polypropylene, polystyrene, nitrocellulose, nylon, glass, quartz, silicones, polyformaldehyde, cellulose, or cellulose acetate. In a preferred embodiment, the multiplicity of nucleic acids (or other moieties) is attached to a single contiguous surface or to a multiplicity of surfaces juxtaposed to each other. In an array format a large number of different hybridization reactions can be run simultaneously. Arrays, particularly nucleic acid arrays can be produced according to a wide variety of methods known to the person of skill, for example by spotting using a pipette or by oligonucleotide synthesis technology. Methods for preparing arrays are described, for example, in Xing, W. L. and Cheng, J. (eds.) Biochips. Technology and Applications, Springer, Berlin 2003.

Aside from hybridization-based assays using labeled probes, amplification of the nucleotide sequence portion of SEQ ID NO:1, for example a sequence located within the coding sequence of ESR1, or a nucleotide sequence having, for example, at least 95% sequence identity to such portion can also be detected by PCR-based methods. Thus according to a further preferred aspect, detecting whether the selected nucleotide sequence portion of SEQ ID NO:1 is amplified comprises a PCR, preferably a quantitative PCR (qPCR). Preferably, the PCR uses at least one primer which hybridizes to the ESR1 coding sequence ranging from nucleotide positions 1048135 to 1343855 of SEQ ID NO:1 or a part thereof.

Protocols for qPCR are known to the person skilled in the art and can be found, for example, in Bartlett and Stirling (2003), PCR Protocols (Methods in Molecular Biology), 2nd edition, Humana Press, Totowa, N.J., USA. Quantitative PCR is a method for multiplying nucleic acid molecules which additionally allows for a quantification of the PCR product. Quantification can be achieved by comparison, after termination of the PCR, of the signal obtained from the product with a standard curve previously generated with control samples from an exogenous sequence of known concentration and/or copy number (see, for example, Bustin, S. A. (2004), A-Z of Quantitative PCR (IUL Biotechnology, No. 5) (Iul Biotechnology Series) International University Line, La Jolla, USA).

Alternatively, an internal standardization using an endogenous housekeeping gene or sequence for calibration purposes may be used as well. In this method, two different genomic sequences are simultaneously co-amplified using two sets of primer pairs in one reaction tube. One sequence belongs to a single copy gene that does not undergo DNA amplifications and serves as an intrinsic reference to measure the relative DNA copy number difference of the test sequence (e.g. the nucleotide sequence portion selected from SEQ ID NO:1 or a nucleotide sequence having, for example, at least 95% sequence identity to such portion). Because in a PCR reaction the amount of DNA product is doubled with each cycle, the total DNA yield at the end of the reaction depends on the amount of template DNA that was initially present in the sample. If the test gene is amplified there will be abundant PCR product of the test gene as compared to the reference gene after PCR. The ratio between the amounts of PCR products of the reference gene and the test gene reflects the copy number difference between the two genes in the tissue sample. Such PCR approach has been described, for example, as double differential polymerase chain reaction (ddPCR) by Brandt B., et al. (1995), Gene 159: 29-34.

Another possibility for quantification resides in the use of a competitive PCR which utilizes an exogenously added standard composed of neutral DNA fragments, flanked by a common target sequence with target specific primers. In this PCR, one set of primers (directed to the target sequence or gene) is used to amplify both the target sequence or gene and the neutral DNA fragment. The neutral DNA fragments compete with the target DNA for the same reagents and thus act as an internal standard. The internal standard is designed to generate a PCR product of a different size than the target gene. The quantitative competitive PCR targets two templates competing for the same primers in the same reaction. By knowing the amount of internal standard added to the reaction, one can determine the amount of target DNA present, in this case the nucleotide sequence selected from SEQ ID NO:1 or a nucleotide sequence having, for example, at least 95% sequence identity to such portion. Different methods and devices may be utilized to determine the amount of PCR products, including gel electrophoresis, capillary electrophoresis, or real time PCR systems.

According to a particular preferred embodiment, detecting whether the selected nucleotide sequence portion of SEQ ID NO:1 is amplified comprises real-time PCR. If real time PCR methods are used, the amount of DNA product may be detected online during the PCR using sequence unspecific fluorescence dyes (e.g. SybrGreen) or sequence specific fluorescence labeled probes (Taqman probes, FRET probes, molecular beacons). Real time quantitative PCR methods are well known to the person of skill and have been described in great detail in the prior art. For an overview, see Bartlett and Stirling (2003), PCR Protocols (Methods in Molecular Biology), 2nd edition, Humana Press, Totowa, N.J., USA.

For the PCR-based methods according to the invention, the oligonucleotide primers used for generating the PCR product are derived from the sequence provided in SEQ ID NO:1 or a nucleotide sequence having, for example, at least 95% sequence identity to such portion. According to a preferred embodiment, at least one primer used in the PCR hybridizes to the ESR1 coding sequence ranging from nucleotide positions 1048135 to 1343855 of SEQ ID NO: 1 or a part thereof. Thus, the primers will generate a product which is located within the ESR1 coding sequence or extends from the ESR1 encoding sequence into the flanking regions. According to a further preferred embodiment, both primers hybridize to the ESR1 coding sequence, which means that the resulting PCR product (i.e. the nucleotide sequence portion selected from SEQ ID NO:1 or a nucleotide sequence having, for example, at least 95% sequence identity to such portion) is completely located within the ESR1 coding sequence.

According to a further preferred embodiment of the invention, the amplification status of the ESR1 gene can be indirectly detected by immunohistochemistry (IHC) using an antibody directed against the estrogen receptor alpha. Immunohistochemical detection of ER expression is performed on tissue sections from proliferative breast disease. A pathologist is required to analyze staining and to distinguish physiological from non-physiological ER expression. Physiological ER expression (normal ESR1 copy number) is characterized by an inhomogeneous staining pattern with different cell nuclei showing different staining intensities. In addition, ER staining is not found in all cell nuclei. In contrast, ESR1 amplified cells exhibit a homogeneous diffuse and uniformly strong staining in all cell nuclei of the proliferative disease.

The invention also relates to an in-vitro method of determining the responsiveness of metastases of a primary tumor which results from breast cancer to anti-estrogen treatment is provided. The method comprises the steps of
a) detecting in a cell sample from said tumor whether a nucleotide sequence portion of the nucleotide sequence of SEQ ID NO:1 or a nucleotide sequence having at least 95% sequence identity to such portion is amplified in the genome of said tumor cells;
b) classifying said metastases as responsive to anti-estrogen treatment, if the nucleotide sequence portion of the nucleotide sequence of SEQ ID NO:1 or a nucleotide sequence having at least 95% sequence identity to such portion is amplified in the genome of said tumor cells.

The present invention demonstrates that no differences between primary breast cancers and their metastases in terms of their ESR1 amplification status exists. All metastases examined in this regard showed ESR1 amplification when derived from a primary tumor showing ESR1 amplification. Similarly, no metastase was observed that exhibited ESR1 amplification when derived from a primary tumor not showing ESR1 amplification. Thus, the ESR1 amplification status of the primary tumor is representative for its metastases. This finding is of importance because adjuvant anti-estrogen treatment targets residual tumors cells and metastases rather than the primary tumor that usually has been surgically removed from the body.

According to a further aspect of the invention, kits are provided, which are suitable for conducting one of the methods explained above. Specifically, the kits include means and reagents for detecting whether a nucleotide sequence portion of SEQ ID NO:1 or a nucleotide sequence having, for example, at least 95% sequence identity to such portion is amplified in a cell sample (or a blood or bone marrow sample). For example, the kit can comprise one or more probes which hybridize to a nucleotide sequence portion of the nucleotide sequence of SEQ ID NO:1 or a nucleotide sequence having, for example, at least 95% sequence identity to such portion. In particular, the probe hybridizes to the ESR1 coding sequence ranging from nucleotide positions 1048135 to 1343855 of SEQ ID NO:1 or a part thereof. Moreover, the kit can comprise further reagents for labeling the probes to allow for the detection of the nucleic acid hybridization complexes. Preferably, reagents for visualizing the complex formed between one or more probes and the target sequence are also provided. According to a further preferred embodiment of the invention, a kit for PCR-based detection methods is provided. Such kit may comprise oligonucleotide primers for generating a PCR product having a sequence comprised by the sequence of SEQ ID NO:1 or a nucleotide sequence having, for example, at least 95% sequence identity to SEQ ID NO:1. Preferably, the kit comprises at least one primer which hybridizes to the ESR1 coding sequence ranging from nucleotide positions 1048135 to 1343855 of SEQ ID NO:1 or a part thereof. It may also comprise one or more polymerase enzymes, buffers, nucleotides and/or dyes suitable for PCR-based reactions, in particular for quantitative PCR or quantitative real-time PCR reactions. Typically, the oligonucleotide primers are about 10 nt, 50 nt, or 100 nt in length, preferably about 15 nt to 40 nt in length. The oligonucleotide primer exhibits a identity to a portion of the sequence shown in SEQ ID NO:1 or a nucleotide sequence having, for example, at least 95% sequence identity to such portion that is sufficient to allow for amplification of the sequence. Typically, the oligonucleotide primer contains at least 6, more usually 8, 10, 15, 20, 30, 40, 45 or 50 contiguous nucleotides of a nucleotide sequence portion of the sequence shown in SEQ ID NO:1 or a nucleotide sequence having, for example, at least 95% sequence identity to such portion, and in particular of the sequence ranging from nucleotide positions 1048135 to 1343855. Oligonucleotide primer or probes may be chemically synthesized.

According to a further aspect, the invention relates to the use of an anti-estrogen compound for the preparation of a medicament for the treatment of a patient having a tumor resulting from a proliferative breast disease, wherein the tumor cells have an amplified ESR1 gene in their genomic DNA, i.e. the genome of the tumor cells exhibit an amplified ESR1 gene. According to a preferred embodiment, the proliferative breast disease is breast cancer. The invention therefore provides, amongst other, a medicament for treating a subgroup of ER-positive breast cancer patients which show an significant increased reaction to anti-estrogen treatment, such as Tamoxifen. As used herein, an anti-estrogen compound is any compound that targets to interfere with the naturally occurring interaction between estrogen and an estrogen receptor, preferably the estrogen receptor alpha. Administration of an anti-estrogen compound results in blocking the signal-transducing function of the estrogen receptor, which effects the estrogen-induced reactions, such as cell proliferation. The anti-estrogen compound may act by competitive inhibition of estrogen binding to an estrogen receptor, preferably the estrogen receptor alpha. When administered in an therapeutically effective amount, anti-estrogen compounds bind to an estrogen receptor, preferably the estrogen receptor alpha, thereby blocking estrogen from binding to the receptor. Anti-estrogen compounds comprise estrogen antagonists, estrogen receptor down-regulators or aromatase inhibitors as described above.

According to a further preferred embodiment, the anti-estrogen compound is an estrogen antagonist as defined above. The estrogen antagonist to be used for preparing the medicament is preferably selected from the group of consisting of Tamoxifen, Raloxifene, Clomifene, Toremifene, Trilostane or functional derivatives thereof. Most preferably, the estrogen antagonist is Tamoxifen or a functional derivative thereof. Alternatively, the anti-estrogen compound to be used for preparing the medicament is an agent which interferes with estrogen synthesis, preferably an aromatase inhibitor. The aromatase inhibitor can be selected from the group of Anastrozole, Letrozole, Formestan, Exemestane or functional derivatives thereof. The estrogen antagonist to be used for preparing the medicament can also be an agent which downregulates expression of an estrogen receptor, preferably the estrogen receptor alpha, such as Fulvestrant or a functional derivative thereof. The compounds can be used according to dosis regimens well known in the art.

The invention will become more evident by the following examples which are solely meant to illustrate the invention, and not intended to limit the invention.

EXAMPLES

Contingency table analysis and Chi-square tests were used to study the relationship between histologic tumor type, grade, stage and gene amplification. Survival curves were plotted according to Kaplan-Meier. A log rank test was applied to examine the relationship between gene amplifications and patient survival.

1. Example 1

Determination of ESR1 Amplification by Array CGH

1.1 Tissues

For array CGH experiments, 30 fresh frozen tissue samples were collected from surgery specimens from the cantonal hospital Basel, Switzerland. All samples were classified by a pathologist as histological grade 3 according to Elston and Ellis (BRE); see Elston, C. W. and Ellis, I. O. (1991), Histopathology 19: 403-410.

1.2 DNA Isolation

For array CGH experiments, genomic DNA was extracted from three punched tissue cylinders (diameter 0.6 mm) from each of the 30 fresh frozen tumor samples according to the manufacturer's instructions of the QIAmp DNA Mini Kit (Qiagen, Hilden, Germany).

1.3 Array-CGH

The extracted DNA obtained from the 30 fresh frozen tumor samples was processed as described in the GeneChip Mapping 10K 2.0 Assay Manual (Affymetrix, Santa Clara, Calif.). All other necessary reagents were provided with the GeneChip Human mapping 10 k Xba assay kit (Affymetrix, Santa Clara, Calif.), and all experimental steps were conducted as described in the GeneChip Mapping 10K 2.0 Assay Manual. Briefly, 250 ng of the DNA were digested with the XbaI restriction enzyme, ligated to an adapter and amplified by PCR. The resulting PCR products were fragmented, end-labeled and hybridized to the GeneChip Human Mapping 10K Array Xba 142 2.0. After hybridization, the microarray chip was washed and stained on an Affymetrix fluidics station. The chips were scanned using the Affymetrix GeneChip scanner 3000.

1.4 Data Acquisition and Analysis

Raw data from the scanned CGH arrays was acquired using the GeneChip Operating Software (Affymetrix). Quality of the data was checked as described in the GeneChip Mapping 10K 2.0 Assay Manual (Affymetrix, Santa Clara, Calif.). Only 22 of the samples passed these quality controls and were used for further data analysis. The data files were imported into the dChip software (Harvard, Boston), and pre-processing and normalization were performed as recommended in the user manual of the software. The resulting signal intensities were imported into Excel. Quartiles were calculated from all signal intensities belonging to one SNP. An average value was calculated from all values lying within the $2^{nd}$ and $3^{rd}$ quartile. This specific value was used as denominator for the calculation of the ratio of each SNP signal of each sample. The resulting ratios were logged (log base 2) and imported into the R suite (R Development Core Team). Using the DNAcopy package (E. S. Venkatraman and A. B. Olshen) of the BioConductor suit of R, change-points in the data were calculated and visualized. Regions with an elevated copy number were classified as amplified regions.

1.5 Results

Amplifications of genomic DNA portions of the tumor cells which include a chromosomal locus comprising the ESR1 gene were identified in 2 (9%) of the 22 successfully analyzed samples. The results of the CGH analysis can be seen in FIG. 1.

2. Example 2

Fluorescence In Situ Hybridization (FISH)

2.1 The general results obtained by CGH were verified by fluorescence in situ hybridization (FISH) using existing tissue microarrays. A breast cancer Prognosis Tissue Microarray containing more than 2517 breast tissues was analyzed. The composition and preparation of this Tissue Microarray (TMA) has been described in detail before (Ruiz, C., et al. (2006), Int J Cancer, 118: 2190-2194; Simon, R., et al. (2004), In: Molecular Diagnosis of Cancer; Roulston J. E., Bartlett J. M. S. (eds.) Humana Press Inc). The type of adjuvant treatment was known for 420 patients. A subset of 261 patients received anti-hormonal treatment by Tamoxifen derivates as the only therapy regimen after surgical removal of the tumor.

2.2 To study ESR1 amplification in non-malignant breast tissues, a second TMA was analyzed containing 73 samples of normal breast tissue and 186 pre-malignant breast tissues, including DCIS (n=62), LCIS (n=10), apocrine metaplasia ((n=14), intraductal hyperplasia (n=27), atypical intraductal hyperplasia (n=5), mastopathy (n=22), papilloma (n=31), and sclerosing adenosis (n=15) (Ruiz, C., et al. (2006), Int J Cancer, 118: 2190-2194).

Additionally, in order to address potential heterogeneity of ESR1 amplification between primary breast tumors and metastases, a third TMA was analyzed containing 815 tissue samples from 160 breast cancer patients. Primary tumors and corresponding metastases were included from 58 patients. Of the remaining 102 patients, no primary tumors (but multiple different metastases) were available. There were 5.0 metastases (range 1-15) on average per patient. Most metastases originated from the lungs (n=106), the liver (n=95), or the bone marrow (n=86). The site of origin had not been recorded in 125 samples.

2.3 The TMA sections were treated according to the Paraffin Pretreatment Reagent Kit protocol (Vysis, Downers Grove, Ill.) before hybridization. FISH was performed with a digoxigenated BAC probe (BAC RP11-450E24, RZPD, Germany) covering part of the ESR1 gene. The sequence of the probe corresponded to the sequence ranging from nucleotide 1.064.232 to nucleotide 1.203.918 of SEQ ID NO:1. As a reference, a Spectrum-Orange labeled chromosome 6 centromeric probe (CEP6) purchased from Vysis was used. Hybridization and posthybridization washes were according to the "LSI procedure" (Vysis). Probe visualization using fluorescent isothiocyanate (FITC)-conjugated sheep anti-digoxigenin (Roche Diagnostics, Rotkreuz, Switzerland) was as described (Wagner, U., et al. (1997), Am J Pathol, 151: 753-759). Slides were counterstained with 125 ng/ml 4',6-diamino-2-phenylindole in an antifade solution. Two different approaches were applied to define amplification. For a first rapid evaluation of the array, signal numbers were estimated for each tissue spot applying predefined criteria: Amplification was defined as presence of more gene signals than centromere signals. All tumors not meeting these criteria were considered non-amplified. In a second more refined analysis FISH signal numbers of the ESR1 gene and centromere 6 were counted in each tissue spot. In accordance to the definition that is recommended for routine diagnostic detection of HER2 amplification in breast cancer (Pathvysion Kit, Abbott Laboratories, North Chicago, Ill., USA), ESR1 copy number changes were subsequently rated according to the ratio of the ESR1 to centromere 6 signal numbers. Amplification was defined as presence of at least two times more ESR1 signals as Cen6 signals (ratio≧2). All other samples were regarded as non-amplified.

2.4 Results

FISH analysis of ESR1 was successful in 1679/2197 (76%) arrayed breast cancer tissues. FISH analysis failed in 518 cases either due to lack of tumor cells in the tissue spot or because of complete loss of tissue spots. When defining amplification as more ESR1 gene signals relative to centromere 6 signals, ESR1 amplification was present in 526/1679 (31%) analyzable tissue samples. ESR1 amplifications were significantly associated with low-stage (pT1, p=0.0416) and low-grade (G1, p<0.0001) tumors. Medullary cancers had a significant lower fraction of amplified tumors (4.2%, p<0.0001) as compared in ductal (32%), lobular (30%), tubular, and cribriform (28%) cancers. In contrast, mucinous cancers showed particularly high rates of ESR1 amplifications (48.6%, p=0.0012). If the definition of amplification was based on the ESR1 to Cen6 signal number ratio, ESR1 amplification (ratio≧2) was found in 20.6% of samples. The same associations between ESR1 amplification and tumor phenotype or patient prognosis were found using this definition of amplification. All associations of ESR1 copy number changes to breast cancer phenotype are summarized in the table provided in FIG. 2A. Using the same breast cancer TMA, amplifications of CCND1 in 20.1%, HER2 in 17.3%, MDM2 in 5.7%, CMYC in 5.3%, and EGFR in 0.8% of the tumors were found previously (Al-Kuraya, K., et al. (2004); Cancer Res, 64: 8534-8540).

Furthermore, by use of the second array containing samples from normal and pre-malignant tissues, ESR1 amplification was found in 15/40 (37%) DCIS, 2/3 (67%) LCIS, 10/23 (43%) papillomas, 3/11 (27%) intraductal hyperplasias, 1 of 2 atypical intraductal hyperplasias, 1/13 (8%) cases with mastopathy, 1/7 (14%) sclerosing adenoses, and 1/30 (3%) histologically normal breast tissue.

A preliminary analysis of the first 50 patients of the third array did not argue for major differences between primary breast cancers and metastases. ESR1 amplification was found in 15/50 (30%) patients. For 20 of these patients, both the primary tumor and at least one metastasis (average 4 metastases, range 1-8) was analyzable. ESR1 amplification was seen in 5 of these primary tumors. All matched metastases (n=20) also showed ESR1 amplification. Of the remaining 15 primary tumors without ESR1 amplification, none of the matched metastases (n=56) had ESR1 amplification.

3. Example 3

Immunohistochemistry 3.1 Immunohistochemical detection of the estrogen receptor alpha protein was performed using the above described TMAs and antibody NCL-L-ER-6F11 as a primary antibody (Novocastra, Newcastle, UK). The TMA slides were deparaffinized and incubated in a pressure cooker at 120° C. for 12 min in pH 6 citrate buffer (Retrievit 6 #BS-1006-00, BioGenex, San Ramon, Calif.). After blocking of endogeneous peroxidase, pre-diluted (1:1000) primary antibody was applied and the slides were incubated overnight at 4° C. The Vectastain ABC Elite system was used for detection of antibody binding. IHC scoring was performed according to the Allred score (Harvey, J. M., et al. (1999), J Clin Oncol, 17: 1474-1481). In brief, intensity of the estrogen receptor staining was recorded in a 4-step scale (0-3) and the fraction of ER positive tumor cells in a 5-step (1-5) scale. Combination of both parameters results in an 8-step score, where all samples with score>2 are regarded as ER positive.

3.2 Results

Immunohistochemical detection of ER expression was successful in 2018/2197 (92%) breast cancers. Like ESR1 amplification, ER expression was linked to low stage (pT1, p=0.002) and low grade (pT1, p<0.0001) cancers. Malignant tumors are classified according to the degree of malignancy of the cell (histological grade, G) and the extension of the tumor (tumor stage, pT). Criteria for the definition of grade are described in Elston, C. W. and Ellis, I. O. (1991), Histopathology 19: 403-410. Criteria for the definition of tumor stage are described in Wittekind C. et al. (2005) Tnm Atlas: Illustrated Guide to the Tnm/Ptnm-Classification of Malignant Tumors. Springer Medizin Verlag Heidelberg. ER expression was also less frequent in medullary (p<0.0001) but more frequent in mucinous cancers (p<0.0001; table 1).

Figure 3:
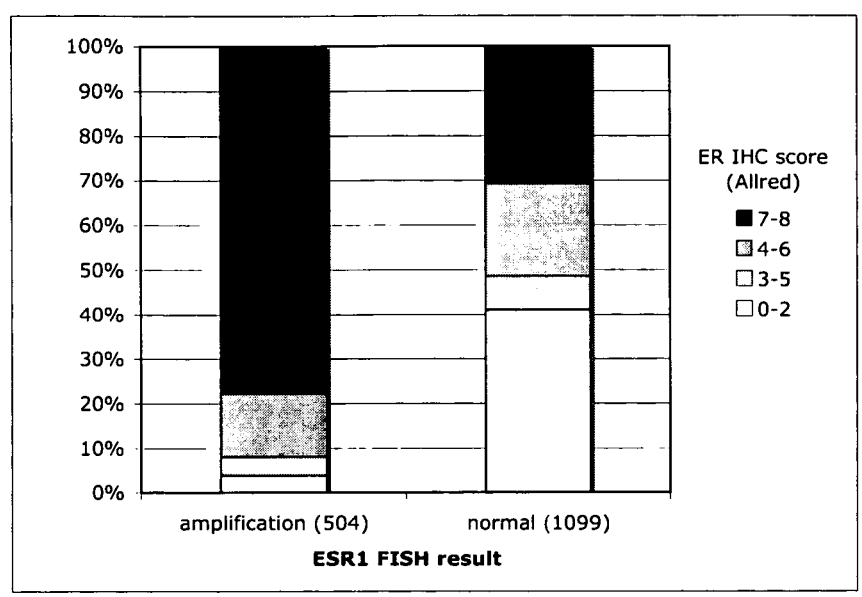
FIG. 3 demonstrates the relationship between ER protein expression and ESR1 amplification.

Relationship between ESR1 amplification and ER protein expression data from a previous unpublished immunohistochemistry experiment were compared with the ESR1 gene copy number state to address the association between ESR1 amplification and protein expression. There was a strong relationship between ESR1 amplifications and ER protein expression (p<0.0001). In 504 breast cancers with ESR1 amplification, 485 (96%) of samples were positive for ER expression. The vast majority of these tumors (78%) had the highest ER scores (7-8) according to Allred (Harvey, J. M., et al. (1999), J Clin Oncol, 17: 1474-1481); see FIG. 3. In contrast, tumors with normal ER copy numbers had only 59% ER IHC positive cases including 31% samples with a score 7-8 ER expression.

4. Example 4

Prognostic Relevance of ESR1 Alterations in Breast Cancer Treated With Tamoxifen 4.1 To address the impact of ESR1 gene amplification on response to anti-estrogen treatment, immunohistochemistry (IHC) data and FISH data were jointly analyzed for the samples of the subset of patients which have been treated with Tamoxifen. For this analysis, IHC data were grouped into ER negative (Allred scores 0-2) and ER positive (Allred scores 3-8, no amplification by FISH), and these groups were compared to a subset of patients with ESR1 amplification (FIG. 4).

4.2 Results

Figure 4:
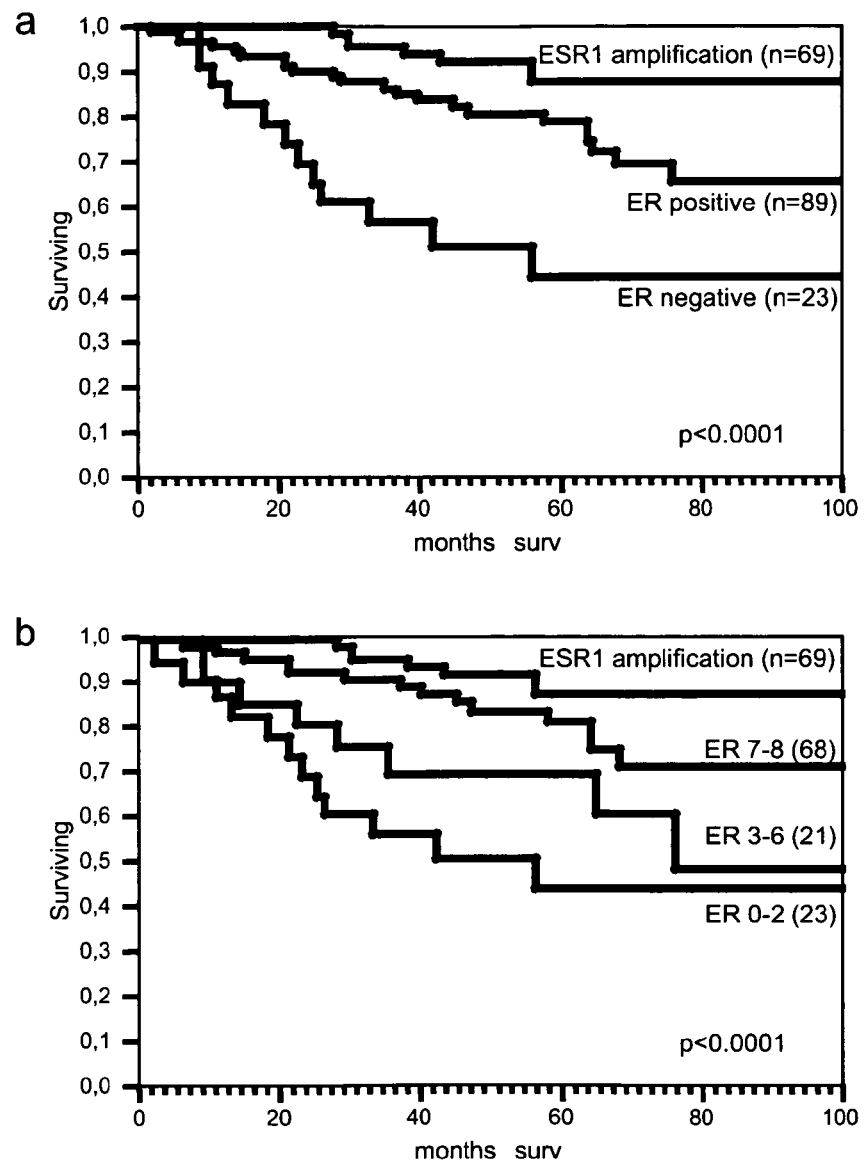
FIG. 4 illustrates the impact of ESR1 amplification and expression on prognosis in patients that received Tamoxifen monotherapy; a) Immunohistochemistry results grouped into negative (scores 0-2) and positive (scores 3-8) according to Allred; b) Immunohistochemistry results by scores.

Surprisingly, the prognosis of Tamoxifen treated patients with ESR1 amplification was significantly better than prognosis of patients that were ER positive by IHC but had no ESR1 gene amplification (FIG. 4, ESR1 amplification versus ER positive: p<0.0001). This difference was also seen between tumor with strong (score 7-8) ER positively and tumors with amplification (p<0.0001). A multivariate analysis including classical predictors of outcome in breast cancer (tumor stage, grade, nodal stage, ER IHC) in the subset of patients that had received Tamoxifen as monotherapy revealed that ESR1 amplification, but not ER expression, was an independent prognosticator of patient prognosis (see table in FIG. 2B). These data strongly suggest that ESR1 amplification may identify a subgroup of ER positive breast cancers with maximal likelihood of a good clinical response to anti-estrogen therapy.

5. Example 5

Association Between ESR1 Amplification and Other Molecular Markers 5.1 For co-amplification/co-expression analysis, data on gene amplification of HER2, EGFR, CMYC, MDM2, and CCND1 (Al-Kuraya, K., et al. (2004); Cancer Res, 64: 8534-8540), as well as p53 expression as detected by immunohistochemistry (Torhorst, J., et al. (2001); Am J Pathol, 159: 2249-2256), were compared to the ESR1 amplification status.

5.2 Results

ESR1 amplification was inversely related to p53 positivity (p=0.0003), and HER2 amplification (p=0.0099). In contrast, there was a positive correlation between amplifications of CCND1 and ESR1 (p=0.05). The amplification status of EGFR, CMCY, and MDM2 was unrelated to ESR1. The significant association with CCND1 amplifications is in concordance with previous studies reporting a strong link between immunohistochemical ER positivity and CCND1 amplification (Naidu, R., et al. (2002); Oncol Rep, 9: 409-416; Seshadri, R., et al. (1996); Clin Cancer Res, 2: 1177-1184). The high frequency of ESR1 amplification in low grade and early stage breast cancer together with the critical role of ER for proliferation control in breast epithelium would be well consistent with a very early—if not initializing—role of ER amplification in a subset of breast cancers.

In summary, these data suggest that ESR1 amplification is a frequent initial event enabling breast epithelial cells to escape growth control. ESR1 amplification defines a significant subtype of untreated primary breast cancers that maximally benefits from anti ER treatment.

6. Example 6

Mapping of the ESR1 Amplicon

In order to estimate the size of the ESR1 amplicon, a small tissue microarray containing 32 samples of breast cancer samples that showed ESR1 amplification using probe RP11-450E24 (which hybridizes within the ESR1 coding sequence; for sequence information, see above) was constructed. The TMA was analyzed in a FISH assay using additional probes which hybridize to sequences in the flanking region of the ESR1 gene. Specifically, the samples were analyzed with FISH probes that either map approximately 1 Mb upstream or 1.2 Mb downstream of the ESR1 gene. Labeling of the probes and evaluation of probe binding were performed as described in example 2 above. The upstream probe (RP1-44A20) corresponds to a sequence starting at base position 1 and ending at base position 165.000 of SEQ ID NO:1. The downstream probe (RP11_306013) corresponds to a sequence starting at base position 2.581.065 and ending at base position 2.725.892 of SEQ ID NO:1.

As a result, amplification of the upstream probe (RP1-44A20) was found in 4 ESR1 amplified tumors. Amplification of the downstream probe (RP11_306013) was confirmed in 1 ESR1 amplified tumor. This results clearly indicated that amplification of the ESR1 gene can be assayed by assessing the amplification status of a nucleotide sequence contained in the SEQ ID NO:1 but not forming part of the ESR1 coding sequence.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08101352B2). An electronic copy of the "Sequence Listing" will also be available from the USPTO upon request and payment of the fee set forth in 37 CFR 1.19(b)(3).

The invention claimed is:

1. An in-vitro method of identifying a tumor resulting from a proliferative breast disease as responsive to anti-estrogen treatment, comprising:
    a) detecting in a cell sample from said tumor whether a nucleotide sequence portion of the nucleotide sequence of SEQ ID NO:1 or a nucleotide sequence having at least 95% sequence identity to such portion is amplified in the genome of said tumor cells;
    b) classifying said tumor as responsive to anti-estrogen treatment, if the nucleotide sequence portion of SEQ ID NO:1 or a nucleotide sequence having at least 95% sequence identity to such portion is amplified in the genome of said tumor cells.

2. An in-vitro method of identifying a candidate patient with a tumor resulting from a proliferative breast disease as suitable for anti-estrogen treatment, comprising:
    a) detecting in a cell sample from said tumor whether a nucleotide sequence portion of the nucleotide sequence of SEQ ID NO:1 or a nucleotide sequence having at least 95% sequence identity to such portion is amplified in the genome of said tumor cells;
    b) classifying said patient as one that is suitable for anti-estrogen treatment, if the nucleotide sequence portion of the nucleotide sequence of SEQ ID NO:1 or a nucleotide sequence having at least 95% sequence identity to such portion is amplified in the genome of said tumor cells.

3. The method according to claim 1 or claim 2, wherein the anti-estrogen treatment comprises administration of an estrogen antagonist.

4. The method according to claim 1 or claim 2, wherein the anti-estrogen treatment comprises administration of an agent which interferes with estrogen synthesis.

5. The method according to claim 4, wherein the agent which interferes with estrogen synthesis is an aromatase inhibitor.

6. The method according to claim 1 or claim 2, wherein the anti-estrogen treatment comprises administration of an agent which downregulates expression of an estrogen receptor.

7. The method according to claim 1 or claim 2, wherein the anti-estrogen treatment is to be performed as a mono-therapy.

8. The method according to claim 1 or claim 2, wherein the proliferative breast disease is selected from the group consisting of ductal hyperplasia, papillomas, sclerosing adenosis, mastopathy, Phylloides tumor, fibroadenoma, DCIS, LCIS and apocrine metaplasia.

9. The method according to claim 1 or claim 2, wherein the proliferative breast disease is breast cancer.

10. The method according to claim 1 or claim 2, wherein said nucleotide sequence portion comprises at least a part of the ESR1 coding sequence ranging from nucleotide positions 1048135 to 1343855 of SEQ ID NO : 1.

11. The method according to claim 10, wherein said nucleotide sequence portion is located within the ESR1coding sequence ranging from nucleotide positions 1048135 to 1343855 of SEQ ID NO:1.

12. The method according to claim 1 or claim 2, wherein detecting whether said nucleotide sequence portion or nucleotide sequence having at least 95% sequence identity to such portion is amplified comprises DNA analysis using a probe which hybridizes to said nucleotide sequence portion or to a nucleotide sequence having at least 95% sequence identity to such portion.

13. The method according to claim 12, wherein the probe hybridizes to the ESR1 coding sequence ranging from nucleotide positions 1048135 to 1343855 of SEQ ID NO : 1 or a part thereof.

14. The method according to claim 12, wherein detecting whether said nucleotide sequence portion or nucleotide sequence having at least 95% sequence identity to such portion is amplified comprises Southern-Blotting.

15. The method according to claim 12, wherein detecting whether said nucleotide sequence portion or nucleotide sequence having at least 95% sequence identity to such portion is amplified comprises fluorescent in-situ hybridization (FISH).

16. The method according to claim 12, wherein detecting whether said nucleotide sequence portion or a nucleotide sequence having at least 95% sequence identity to such portion is amplified comprises a polymerase chain reaction (PCR).

17. The method according to claim 16, wherein the PCR uses at least one primer which hybridizes to the ESR1 coding sequence ranging from nucleotide positions 1048135 to 1343855 of SEQ ID NO : 1 or a part thereof.

18. The method according to claim 16, wherein detecting whether said nucleotide sequence portion or nucleotide sequence having at least 95% sequence identity to such portion is amplified comprises quantitative PCR.

19. The method according to claim 18, wherein detecting whether said nucleotide sequence portion or nucleotide sequence having at least 95% sequence identity to such portion is amplified comprises quantitative real-time PCR.

* * * * *